United States Patent [19]
Dreyfus et al.

[11] Patent Number: 5,959,074
[45] Date of Patent: Sep. 28, 1999

[54] PRODUCTS AND PROCESSES FOR REGULATION OF GENE RECOMBINATION

[75] Inventors: David H. Dreyfus, Denver; Erwin W. Gelfand, Englewood, both of Colo.

[73] Assignee: National Jewish Medical and Research Center, Denver, Colo.

[21] Appl. No.: 08/807,332

[22] Filed: Feb. 28, 1997

Related U.S. Application Data

[60] Provisional application No. 60/012,616, Mar. 1, 1996, and provisional application No. 60/023,064, Aug. 2, 1996.

[51] Int. Cl.$^6$ ..................................................... C07K 14/00
[52] U.S. Cl. .......................................... 530/300; 530/324
[58] Field of Search ................................... 530/300, 324, 530/325, 326, 327, 328, 329, 330, 350

[56] References Cited

U.S. PATENT DOCUMENTS 5,159,066  10/1992  Schatz et al. ........................... 536/23.2

OTHER PUBLICATIONS

Schatz et al, Cell, vol. 59, pp. 1035–1048, Dec. 22, 1989.
Luckow et al, Molecular and Cellular Biology, vol. 14(3), pp. 1626–1634, Mar. 1994.
Ngo et al, The Protein Folding Problem and Tertiary Structure Prediction, Mertz et al (eds), Birkhauser, Boston, pp. 492–495, 1994.
Heierhorst et al, PNAS(USA), vol. 89, pp. 6798–6802, Aug. 1992.
Alam et al, J. of Bacteriology, vol. 173(18), pp. 5778–5783, Sep. 1991.
Albrecht et al, J. of Virology, vol. 66(8), pp. 5047–5058, Aug. 1992.
Cuomo et al., 1994, *Nucleic Acids Res.*, 22(10):1810–1814.
de Bruyn Kops et al., 1988, *Cell*, 55:857–868.
Doak et al., 1994, *Proc. Natl. Acad. Sci USA*, 91:942946.
Dreyfus, 1992, *Molecular Immunology*, 29(6):807–810.
Dyda et a l., 1994, *Science*, 266:1981–1986.
Gao et al., 1989, *J. of Virol.*, 63(12):5258–5267.
van Gent et al., 1996, *Science*, 271:1592–1594.
Morrison et al., 1996, *Virology*, 220:402–413.
Oettinger et al., 1990, *Science*, 248:1517–1523.
Rodgers et al., 1996, JMB,33:pp. 70–84.
Sadofsky et al., 1994, *Nucleic Acids Res.*, 22(10):1805–1809.
Silver et al., 1993, *Proc. Natl. Acad. Sci.*, 90:6100–6104.
Thompson et al., 1995, *Immunity*, 3:531–539.
van Luenen et al., 1994, *Cell*, 79:293–301.

*Primary Examiner*—Terry McKelvey
*Attorney, Agent, or Firm*—Sheridan Ross P.C.

[57] ABSTRACT

This invention generally relates to a novel recombinogenic motif having transposase activities that is important to the regulation and function of Herpes virus replication, V(D)J recombination, and immunoglobulin class switching. The present invention also relates to a site-specific DNA binding region for V(D)J and V(D)J-like recombination signals. Disclosed are identifying characteristics of such motifs as well as methods for identifying the motifs.

2 Claims, 3 Drawing Sheets

A) Putative RAG1 (R1)/RAG2 (R2) heteromeric complex.

B) Putative DBP homodimeric complex.

SEQUENCE LISTING (1) GENERAL INFORMATION:

(iii) NUMBER OF SEQUENCES: 32

(2) INFORMATION FOR SEQ ID NO:1:

(i) SEQUENCE CHARACTERISTICS:
       (A) LENGTH: 45 amino acids
       (B) TYPE: amino acid
       (C) STRANDEDNESS:
       (D) TOPOLOGY: linear (ii) MOLECULE TYPE: peptide (xi) SEQUENCE DESCRIPTION: SEQ ID NO:1:

Asp Asn Xaa Xaa Xaa His Xaa Ser Arg Lys Xaa Arg Xaa Trp Leu Lys
   1               5                   10                  15

Xaa Xaa Xaa Xaa Xaa Xaa Xaa Xaa Xaa Xaa Lys Val Xaa Leu Leu
               20                  25                  30

Xaa Xaa Pro Ser Xaa Ser Pro Asp Leu Asn Pro Ile Glu
           35                  40                  45

(2) INFORMATION FOR SEQ ID NO:2:

(i) SEQUENCE CHARACTERISTICS:
       (A) LENGTH: 37 amino acids
       (B) TYPE: amino acid
       (C) STRANDEDNESS:
       (D) TOPOLOGY: linear (ii) MOLECULE TYPE: peptide (ix) FEATURE:
       (A) NAME/KEY: Peptide
       (B) LOCATION: 1
       (D) OTHER INFORMATION: /note= "X = D or E at first and
           last positions"

(xi) SEQUENCE DESCRIPTION: SEQ ID NO:2:

Xaa Asn Xaa Xaa Xaa Xaa Xaa Ser Xaa Xaa Xaa Trp Leu Lys Xaa Xaa
   1               5                   10                  15

Xaa Xaa Xaa Xaa Xaa Xaa Xaa Xaa Xaa Xaa Xaa Ala Xaa Xaa Gly Xaa
               20                  25                  30

Leu Xaa Ala Xaa Xaa
           35

(2) INFORMATION FOR SEQ ID NO:3:

(i) SEQUENCE CHARACTERISTICS:
       (A) LENGTH: 24 amino acids
       (B) TYPE: amino acid
       (C) STRANDEDNESS:
       (D) TOPOLOGY: linear (ii) MOLECULE TYPE: peptide (xi) SEQUENCE DESCRIPTION: SEQ ID NO:3:

Asp Asn His Ser Arg Lys Arg Trp Leu Lys Val Leu Leu Pro Ser
   1               5                   10                  15

Ser Pro Asp Leu Asn Pro Ile Glu
               20

(2) INFORMATION FOR SEQ ID NO:4:

(i) SEQUENCE CHARACTERISTICS:

(A) LENGTH: 20 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:4:

Asp Asn Ser His Ser Arg Arg Gln Ile Leu Pro Tyr Ser Pro Gln Leu
    1               5                   10                  15

Asn Ile Glu Glu
                20

(2) INFORMATION FOR SEQ ID NO:5:

(i) SEQUENCE CHARACTERISTICS:
          (A) LENGTH: 40 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:5:

Glu Asn Asp Asn Pro Gly Leu Gly Gln Ser Pro Pro Glu Trp Leu Lys
    1               5                   10                  15

Gly His Tyr Gln Thr Leu Cys Thr Asn Phe Arg Ser Leu Ala Ile Asp
                    20                  25                  30

Lys Gly Val Leu Thr Ala Lys Glu
                35                  40

(2) INFORMATION FOR SEQ ID NO:6:

(i) SEQUENCE CHARACTERISTICS:
          (A) LENGTH: 38 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:6:

Glu Asn Pro Ala Val Gly Val Ser Pro Gly Glu Trp Leu Lys Met His
    1               5                   10                  15

Tyr Gln Thr Leu Trp Thr Asn Phe Lys Asn Ser Cys Ile Asp Lys Gly
                    20                  25                  30

Val Leu Thr Gly Thr Glu
                35

(2) INFORMATION FOR SEQ ID NO:7:

(i) SEQUENCE CHARACTERISTICS:
          (A) LENGTH: 38 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:7:

Asp Asn Pro Leu Thr Thr Ala Gln Ile Ser Ala Trp Val Thr Leu His
    1               5                   10                  15

Phe Gln Ser Ile Cys Gly Ala Phe Gly Thr Thr Pro Leu Lys Lys Gly
                    20                  25                  30

Phe Leu Asn Val Lys Asp
                35

(2) INFORMATION FOR SEQ ID NO:8:

(i) SEQUENCE CHARACTERISTICS:
        (A) LENGTH: 46 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

```
Asp Arg Pro Cys Thr Gly Asn Ser Ile Ser Lys Val Leu Val Gln Gln
1               5                  10                  15

Tyr Gln Ser Leu Tyr Gly Thr Phe His Ser Ser Tyr Leu Lys Lys Gly
            20                  25                  30

Phe Leu Asn Thr Arg Thr Val Lys Val Ala Ser Asn Val Asp
        35                  40                  45
```

(2) INFORMATION FOR SEQ ID NO:9:

(i) SEQUENCE CHARACTERISTICS:
        (A) LENGTH: 35 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

```
Asp Pro Leu Gly Asn Tyr Ala Pro Tyr Leu Ile Leu Arg Lys Pro Gly
1               5                  10                  15

Asp Gln Thr Glu Ala Ala Lys Ala Thr Met Gln Asp Thr Tyr Arg Ala
            20                  25                  30

Thr Leu Glu
        35
```

(2) INFORMATION FOR SEQ ID NO:10:

(i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

```
Asp Val Leu Gly Asn Tyr Ala Ala Phe Ser Ala Leu Lys Arg Ala Asp
1               5                  10                  15

Gly Ser Glu Thr Ala Arg Thr Ile Met Gln Glu Thr Tyr Arg Ala Ala
            20                  25                  30

Thr Glu
```

(2) INFORMATION FOR SEQ ID NO:11:

(i) SEQUENCE CHARACTERISTICS:
        (A) LENGTH: 38 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:11:

```
Asp Gly Leu Ser Gly Leu Ala Ser Ser Val Asp Glu Tyr Pro Val Asp
```

```
           1               5              10              15
       Thr Ile Ala Lys Arg Phe Arg Tyr Asp Ser Ala Leu Val Ser Ala Leu
                        20              25              30

Met Asp Met Glu Glu Asp
                        35
```

(2) INFORMATION FOR SEQ ID NO:12:

(i) SEQUENCE CHARACTERISTICS:
        (A) LENGTH: 38 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:12:

```
       Asp Gly Leu Ser Phe His Val Ser Ile Ala Arg Asn Asp Thr Val Tyr
       1               5              10              15

Ile Leu Gly Gly His Ser Leu Ala Asn Asn Ile Arg Pro Ala Asn Leu
                        20              25              30

Tyr Arg Ile Arg Val Asp
                        35
```

(2) INFORMATION FOR SEQ ID NO:13:

(i) SEQUENCE CHARACTERISTICS:
        (A) LENGTH: 37 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:13:

```
       Asp Asn Gly Pro Ala Phe Val Ser Lys Val Ser Gln Thr Val Ala Asp
       1               5              10              15

Leu Leu Gly Ile Asp Trp Lys Leu His Cys Ala Tyr Arg Pro Gln Ser
                        20              25              30

Ser Gly Gln Val Glu
                        35
```

(2) INFORMATION FOR SEQ ID NO:14:

(i) SEQUENCE CHARACTERISTICS:
        (A) LENGTH: 37 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:14:

```
       Asp Asn Gly Arg Glu Tyr Leu Ser Asn Glu Met Arg Gln Phe Cys Val
       1               5              10              15

Lys Lys Gly Ile Ser Tyr His Leu Thr Val Pro His Thr Pro Gln Leu
                        20              25              30

Asn Gly Val Ser Glu
                        35
```

(2) INFORMATION FOR SEQ ID NO:15:

(i) SEQUENCE CHARACTERISTICS:
        (A) LENGTH: 19 amino acids
        (B) TYPE: amino acid (C) STRANDEDNESS:
        (D) TOPOLOGY: linear (ii) MOLECULE TYPE: peptide (xi) SEQUENCE DESCRIPTION: SEQ ID NO:15:

Asp Gly Phe Val Ser Arg Gln Thr Val Leu Gly His Leu Arg Pro Gln
1               5                   10                  15

Leu Val Glu (2) INFORMATION FOR SEQ ID NO:16:

(i) SEQUENCE CHARACTERISTICS:
        (A) LENGTH: 37 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:16:

Asp Asn Gly Ser Asn Phe Thr Ser Ala Ala Val Lys Ala Ala Cys Trp
1               5                   10                  15

Trp Ala Gly Ile Lys Gln Glu Phe Gly Ile Pro Tyr Asn Pro Gln Ser
            20                  25                  30

Gln Gly Val Val Glu
        35

(2) INFORMATION FOR SEQ ID NO:17:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..25
        (D) OTHER INFORMATION: /label= oligonucleotide (xi) SEQUENCE DESCRIPTION: SEQ ID NO:17:

GGTGGGATCC ACGGGCAGCT ACGTG                                       25

(2) INFORMATION FOR SEQ ID NO:18:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..26
        (D) OTHER INFORMATION: /label= oligonucleotide (xi) SEQUENCE DESCRIPTION: SEQ ID NO:18:

CGGGGATCAT TCTCATAGCA CATACA                                      26

(2) INFORMATION FOR SEQ ID NO:19:

(i) SEQUENCE CHARACTERISTICS:
        (A) LENGTH: 14 amino acids
        (B) TYPE: amino acid (C) STRANDEDNESS:
        (D) TOPOLOGY: linear (ii) MOLECULE TYPE: peptide (xi) SEQUENCE DESCRIPTION: SEQ ID NO:19:

Cys Ser Leu Cys Glu Gly Arg Ala Pro Ala Val Cys Leu Asn
    1               5                   10

(2) INFORMATION FOR SEQ ID NO:20:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..30
        (D) OTHER INFORMATION: /label= oligonucleotide (xi) SEQUENCE DESCRIPTION: SEQ ID NO:20:

ACAAGGATCC ATGTCCCTGC AGATGGTAAC                                          30

(2) INFORMATION FOR SEQ ID NO:21:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..33
        (D) OTHER INFORMATION: /label= oligonucleotide (xi) SEQUENCE DESCRIPTION: SEQ ID NO:21:

CATCGAATTC TTCTGGGAGA ATATATGATG GAG                                      33

(2) INFORMATION FOR SEQ ID NO:22:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..28
        (D) OTHER INFORMATION: /label= oligonucleotide (xi) SEQUENCE DESCRIPTION: SEQ ID NO:22:

CACAGTGCTA CAGACTGGAA CAAAAACC                                            28

(2) INFORMATION FOR SEQ ID NO:23:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(ix) FEATURE:
            (A) NAME/KEY: misc_feature
            (B) LOCATION: 1..28
            (D) OTHER INFORMATION: /label= oligonucleotide (xi) SEQUENCE DESCRIPTION: SEQ ID NO:23:

GGTTTTTGTT CCAGTCTGTA GCACTGTG                                              28

(2) INFORMATION FOR SEQ ID NO:24:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 1..39
            (D) OTHER INFORMATION: /label= oligonucleotide (xi) SEQUENCE DESCRIPTION: SEQ ID NO:24:

CACAGTGGTA GTACTCCACT GTCTGGCTGT ACAAAAACC                                   39

(2) INFORMATION FOR SEQ ID NO:25:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 1..39
            (D) OTHER INFORMATION: /label= oligonucleotide (xi) SEQUENCE DESCRIPTION: SEQ ID NO:25:

GGTTTTTGTA CAGCCAGACA GTGGAGTACT ACCACTGTG                                   39

(2) INFORMATION FOR SEQ ID NO:26:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 1..28
            (D) OTHER INFORMATION: /label= oligonucleotide (xi) SEQUENCE DESCRIPTION: SEQ ID NO:26:

GGTGACACAG GCAACCCTGA CAAAGCCC                                               28

(2) INFORMATION FOR SEQ ID NO:27:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(ix) FEATURE:
    (A) NAME/KEY: misc_feature
    (B) LOCATION: 1..28
    (D) OTHER INFORMATION: /label= oligonucleotide (xi) SEQUENCE DESCRIPTION: SEQ ID NO:27:

GGGCTTTGTC AGGGTTGCCT GTGTCACC                                    28

(2) INFORMATION FOR SEQ ID NO:28:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..36
        (D) OTHER INFORMATION: /label= oligonucleotide (xi) SEQUENCE DESCRIPTION: SEQ ID NO:28:

CACAGGCAAC CCTGACAAAG GCCCCCCAGG AAAGAT                            36

(2) INFORMATION FOR SEQ ID NO:29:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..32
        (D) OTHER INFORMATION: /label= oligonucleotide (xi) SEQUENCE DESCRIPTION: SEQ ID NO:29:

TTGAAGCTTG AGTAAAGTGT AACATTTAAT GT                                32

(2) INFORMATION FOR SEQ ID NO:30:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..19
        (D) OTHER INFORMATION: /label= oligonucleotide (xi) SEQUENCE DESCRIPTION: SEQ ID NO:30:

GGTCTCTAGA CCTCGAGTC                                               19

(2) INFORMATION FOR SEQ ID NO:31:

(i) SEQUENCE CHARACTERISTICS:
        (A) LENGTH: 38 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:31:

```
Asp Asn Pro Ser Ile Gly Met Met Pro Ser Glu Trp Leu Lys Val His
1               5                   10                  15

Tyr Gln Thr Ile Trp Thr Asn Phe Lys Ser Ser Cys Leu Asp Arg Gly
            20                  25                  30

Val Leu Thr Gly Ser Glu
            35
```

(2) INFORMATION FOR SEQ ID NO:32:

(i) SEQUENCE CHARACTERISTICS:
        (A) LENGTH: 40 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:32:

```
Asp Leu Asn Pro Tyr Ala Val Ala Phe Gln Pro Leu Leu Ala Tyr Ala
1               5                   10                  15

Tyr Phe Arg Ser Val Phe Tyr Val Ile Gln Asn Val Ala Leu Ile Thr
            20                  25                  30

Ala Thr Ala Ser Tyr Ile Val Asp
            35                  40
```

PRODUCTS AND PROCESSES FOR REGULATION OF GENE RECOMBINATION

CROSS REFERENCE TO RELATED APPLICATIONS

The present application claims priority from U.S. Provisional Application Ser. No. 60/012,616, filed Mar. 1, 1996, and from U.S. Provisional Application Ser. No. 60/023,064, filed Aug. 2, 1996.

GOVERNMENT RIGHTS

This invention was made in part with government support under NIH grants A129704, A126490, and P01-A129903.

FIELD OF THE INVENTION

The present invention relates to a recombinogenic motif capable of transposase activities that is important to the regulation and function of Herpes virus replication, V(D)J recombination, and immunoglobulin class switching which can be used to develop immunosuppressant and anti-viral agents. The present invention also relates to a site-specific DNA binding region for V(D)J and V(D)J-like recombination signals.

BACKGROUND OF THE INVENTION

Recently, a motif shared between retroviral integrases and invertebrate transposase molecules, termed the D35E motif, has been identified. This motif is partially characterized by the first and last amino acid residues of the motif, which are an aspartate (D) and a glutamate (E), respectively. In most transposases that have been characterized, the spacing between the D and E residues is 35 amino acids, however this interval is not absolutely conserved, with spacings of 34 and 39 amino acids also having been identified. This motif is putatively involved in strand cleavage and transfer of targeted DNA, while site-specificity is conferred by a separate region of the molecule.

Progress has been made in understanding the mechanism of invertebrate transposition and retroviral integration to the point that this common D35E catalytic site has been defined in both processes, which in the case of the Tc elements of *C. elegans* has been shown to be a functional requirement for site-specific recombination.

Viruses such as Herpes viruses and the V(D)J recombination pathway of higher vertebrates undergo regulated site-specific recombination. Similarities between terminal and recombination signal sequences suggest that both the Herpes viruses and the immunoglobulin recombination pathway share a conserved recombination mechanism.

In the case of the Herpes viruses, the virus enters the cell in a linear form, which subsequently circularizes to enter a latent state. Following activation of the lytic cycle, the covalently closed genome then replicates via a putative "rolling circle" to yield concatameric intermediates which are then cleaved into infectious linear monomers. The molecules responsible for the Herpes virus recombination events have not been identified. There is no current description of the mechanism that Herpes viruses utilize to form the viral episome from the linear infectious form during the establishment of latency.

In vertebrates, expression of the recombinase activating gene (RAG) proteins has been identified as both necessary and sufficient to direct V(D)J recombination. In this recombination, a regulated series of site-specific recombinations occurs during development of the T and B cell lineages utilizing an interaction between "V(D)J signals" and the recombinase activating genes (RAG), RAG-1 and RAG-2. While it is known that V(D)J recombination is controlled by recombinase activating genes, the mechanism of V(D)J recombination on a molecular level is not understood.

There is a wide spectrum of need for methods and materials to control recombination events of viruses and the immune response. Interaction between recombinogenic viruses such as Herpes viruses and recombinogenic components of the immune system is in fact problematic. However, the complexity of viral life cycles and of the molecular recombination mechanisms in the immune response have hindered development of such methods and materials. Prior to the present invention, a critical component involved in recombination in non-retroviral viral life cycles and in the immune system of higher vertebrates was not appreciated. Thus, there remains a need to elucidate this component and to develop reagents and methods that would have important implications for viral infection related to pathogenesis and autoimmunity, as well as applications for gene therapy and vaccine development.

SUMMARY OF THE INVENTION

The present invention generally relates to the identification and use of peptides derived from a recombinogenic motif that is capable of transposase activities. Such a motif is important to the regulation and function of Herpes virus replication, V(D)J recombination, retroviral integrase function and immunoglobulin class switching, and can be used to develop immunosuppressant, anti-viral agents, and vectors for gene therapy.

Another embodiment of the present invention relates to the identification and use of a site-specific DNA binding region for V(D)J and V(D)J-like recombination signal sequences.

One embodiment of the present invention relates to a method to identify whether a first amino acid sequence includes a recombinogenic amino acid sequence. This method includes the steps of (a) searching the first amino acid sequence to identify at least one amino acid sequence comprising an initial aspartate or glutamate which is followed at least about 30 amino acid residues downstream by a terminal aspartate or glutamate; (b) generating randomizations of at least one of the amino acid sequences; and (c) aligning at least one of the randomizations with a second amino acid sequence to identify at least one first alignment wherein the probability of the first alignment occurring is not consistent with chance. The second amino acid sequence can be a D35E amino acid consensus sequence or a first D35E amino acid sequence. This method can further include the step of identifying second alignments between the first alignment and a second D35E amino acid sequence. This second D35E amino acid sequence can be derived from an organism category which includes a family, genus, or species. This step of identifying includes maximizing sequence similarity between the first alignment and the second D35E sequence using amino acid similarity default values. The default values include the following groups: (i) neutral/weakly hydrophobic residues which include the amino acid residues P, A, G, S and T; acidic/hydrophilic residues which include the amino acid residues Q, N, E, B, D and Z; basic/hydrophilic residues which include the amino acid residues H, K and R; hydrophobic/aliphatic residues which include the amino acid residues L, I, V and M; hydrophobic/aromatic residues which include the amino acid residues F, Y, and W; and C residues. As used herein, the residues designated by single letters use the standard one-letter nomenclature for amino acid residues known in the art.

One embodiment of the present invention relates to a method to identify whether a first nucleic acid sequence includes a recombinogenic nucleic acid sequence. This method includes the steps of (a) searching the first nucleic acid sequence to identify at least one nucleic acid sequence that encodes an amino acid sequence comprising an initial aspartate or glutamate which is followed at least about 30 amino acid residues downstream by a terminal aspartate or glutamate; (b) generating randomizations of at least one of the nucleic acid sequences; and (c) aligning at least one of the randomizations with a second nucleic acid sequence encoding a second amino acid sequence to identify at least one first alignment wherein the probability of the first alignment occurring is not consistent with chance. The second amino acid sequence can be a D35E amino acid consensus sequence or a first D35E amino acid sequence. This method can further include the step of identifying second alignments between the first alignment and a second D35E nucleic acid sequence. This second D35E nucleic acid sequence can be derived from an organism category which includes a family, genus, or species. This step of identifying includes maximizing sequence similarity between the first alignment and the second nucleic acid sequence using similarity default values for the amino acid residues encoded by the nucleic acid sequences. The default values include the following groups: (i) neutral/weakly hydrophobic residues which include the amino acid residues P, A, G, S and T; acidic/hydrophilic residues which include the amino acid residues Q, N, E, B, D and Z; basic/hydrophilic residues which include the amino acid residues H, K and R; hydrophobic/aliphatic residues which include the amino acid residues L, I, V and M; hydrophobic/aromatic residues which include the amino acid residues F, Y, and W; and C residues.

Another embodiment of the present invention relates to an isolated amino acid molecule which includes a first amino acid sequence. This first amino acid sequence can include a higher vertebrate amino acid sequence or a non-retroviral viral amino acid sequence. Such a first amino acid sequence has at least one identifying characteristic selected from the group of (a) two amino acid residues which include aspartate and glutamate, the residues being separated by at least about 30 amino acid residues; or (b) an ability to align with a second amino acid sequence which includes a D35E amino acid consensus sequence or a first D35E amino acid sequence. In a further embodiment, the first amino acid sequence aligns with a second D35E amino acid sequence in accordance with similarity default values selected from the groups of similarity default values as previously described herein. In another embodiment, the above-described isolated molecule can be further characterized as including a first amino acid sequence having the motif denoted herein as SEQ ID NO:2, which is a motif which the present inventors have determined defines a general motif for a recombinogenic amino acid sequence as described herein. In another embodiment, this motif has consensus residues denoted by underlining the particular consensus residues in the motif as follows: *N_XXXXXS_XXXWL_K_XXXXXXXXXXXXXAXX_G_XL_XAX*.

In other embodiments, the first D35E amino acid sequence includes, but is not limited to, the sequences denoted herein as SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:31 and SEQ ID NO:32. In another embodiment, the D35E consensus sequence is the sequence denoted as SEQ ID NO:1.

Another embodiment of the present invention relates to an isolated nucleic acid molecule which includes a nucleic acid sequence encoding a site-specific DNA binding sequence. The DNA binding sequence has at least one identifying characteristic which include (a) an association with recombinogenic activity; (b) an ability to bind V(D)J and V(D)J-like recombination signal sequences; (c) a location of between about 1 and about 200 amino acids upstream of the carboxyl-terminal end of a recombinogenic amino acid sequence that aligns substantially with a D35E amino acid consensus sequence; or (d) an association with a divalent cation binding region. In a further embodiment, the site-specific DNA binding sequence can include a RAG-1 site-specific DNA binding sequence, a RAG-2 site-specific DNA binding sequence, a Herpes virus site-specific DNA binding sequence, and a retroviral site-specific DNA binding sequence. In another embodiment, such a nucleic acid sequence is operatively linked to an expression molecule to form a recombinant molecule. In a preferred embodiment, such a recombinant molecule includes the recombinant molecules denoted herein as pBA501/304, pBA505/305, pBA506/306, pR2502/302 and pBA5001/3001.

Other aspects and embodiments of the present invention will become obvious to one of ordinary skill in the art after consideration of the drawings and detailed description provided below.

DETAILED DESCRIPTION OF THE INVENTION

Figure 1:
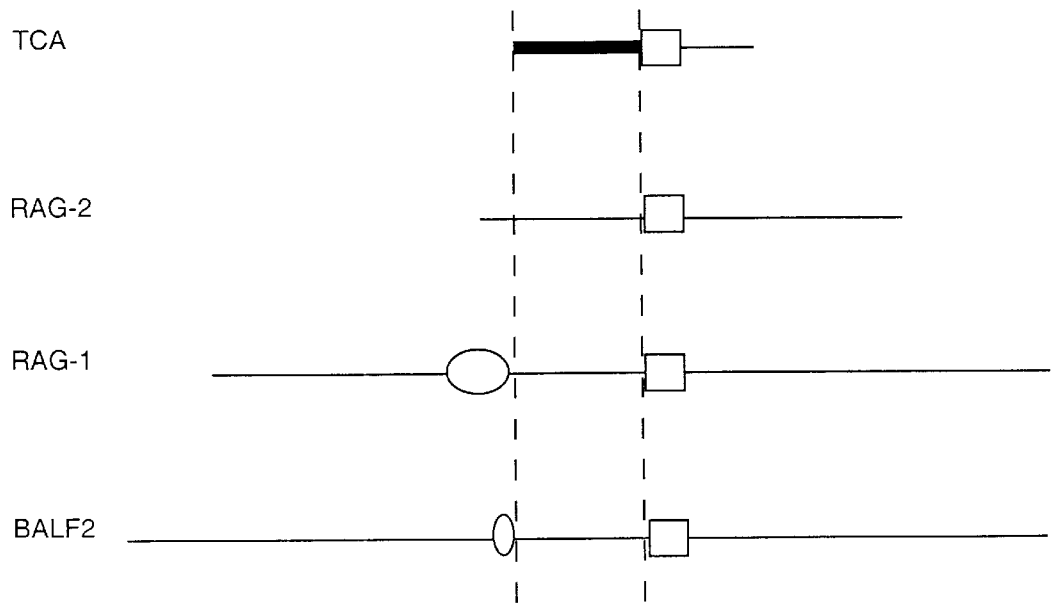
FIG. 1 is a schematic drawing showing regions of BALF2 and RAG proteins aligned with the site-specific binding region of the Tcl transposase.

The present invention generally relates to a recombinogenic motif that is capable of transposase activities. The present invention also relates to a site-specific DNA binding region for V(D)J and V(D)J-like recombination signals that is associated with such a recombinogenic motif. This motif and DNA binding region are important to the regulation and function of Herpes virus replication, V(D)J recombination, and immunoglobulin class switching which can be used to develop immunosuppressant and anti-viral agents.

Phylogenetic analysis, as well as more recent analysis of the mechanism of V(D)J recombination supports the origin of V(D)J recombination via insertion of a transposon-like mobile sequence into the vertebrate genome. However, this analogy has not proven useful in understanding the mechanism of V(D)J recombination at a molecular level. No specific similarity has been identified between factors involved in V(D)J recombination and factors involved in mobile element transposition.

Recently, a motif shared between vertebrate and invertebrate transposase molecules, termed the D35E motif, has been identified. In most transposases characterized the spacing between D and E residues is 35 amino acids, however this interval is not absolutely conserved, with spacings of 34 and 39 amino acids also identified. Both invertebrate and vertebrate mobile elements as well as retroviral integrases contain this highly conserved motif, which in the case of the Tc elements of *C. elegans* has been shown to be a functional requirement for site-specific recombination. This motif is putatively involved in strand cleavage and transfer of targeted DNA, while site-specificity is conferred by a separate region of the molecule.

Both the Herpes viruses and the V(D)J recombination pathway of higher vertebrates also undergo regulated site-specific recombination. In the case of the Herpes viruses, the virus enters the cell in a linear form, which subsequently circularizes to enter a latent state. Following activation of the lytic cycle, the covalently closed genome then replicates via a putative "rolling circle" to yield concatameric intermediates which are then cleaved into infectious linear monomers. While the molecules responsible for the Herpes virus recombination events have not been identified, some evidence suggests that sequences in the terminal repeats of the virus are important in directing the recombination pathway.

In the case of V(D)J recombination, a regulated series of site-specific recombinations occurs during development of the T and B cell lineages utilizing an interaction between V(D)J signals and the recombinase activating genes RAG-1 and RAG-2. The present inventors show herein that there is a similarity between both the mechanism of V(D)J recombination and the Tc transposons based upon shared target sequences and recombination intermediates.

One embodiment of the present invention relates to a method to identify whether a first amino acid sequence includes a recombinogenic amino acid sequence. This method includes the steps of (a) searching the first amino acid sequence to identify at least one amino acid sequence comprising an initial aspartate or glutamate which is followed at least about 30 amino acid residues downstream by a terminal aspartate or glutamate; (b) generating randomizations of at least one of the amino acid sequences; and (c) aligning at least one of the randomizations with a second amino acid sequence to identify at least one first alignment wherein the probability of the first alignment occurring is not consistent with chance. The second amino acid sequence can be a D35E amino acid consensus sequence or a first D35E amino acid sequence. This method can further include the step of identifying second alignments between the first alignment and a second D35E amino acid sequence. This second D35E amino acid sequence can be derived from an organism category which includes a family, genus, or species. This step of identifying includes maximizing sequence similarity between the first alignment and the second D35E sequence using amino acid similarity default values. The default values include the following groups: (i) neutral/weakly hydrophobic residues which include the amino acid residues P, A, G, S and T; acidic/hydrophilic residues which include the amino acid residues Q, N, E, B, D and Z; basic/hydrophilic residues which include the amino acid residues H, K and R; hydrophobic/aliphatic residues which include the amino acid residues L, I, V and M; hydrophobic/aromatic residues which include the amino acid residues F, Y, and W; and C residues.

One embodiment of the present invention relates to a method to identify whether a first nucleic acid sequence includes a recombinogenic nucleic acid sequence. This method includes the steps of (a) searching the first nucleic acid sequence to identify at least one nucleic acid sequence that encodes an amino acid sequence comprising an initial aspartate or glutamate which is followed at least about 30 amino acid residues downstream by a terminal aspartate or glutamate; (b) generating randomizations of at least one of the nucleic acid sequences; and (c) aligning at least one of the randomizations with a second nucleic acid sequence encoding a second amino acid sequence to identify at least one first alignment wherein the probability of the first alignment occurring is not consistent with chance. The second amino acid sequence can be a D35E amino acid consensus sequence or a first D35E amino acid sequence. This method can further include the step of identifying second alignments between the first alignment and a second D35E nucleic acid sequence. This second D35E nucleic acid sequence can be derived from an organism category which includes a family, genus, or species. This step of identifying includes maximizing sequence similarity between the first alignment and the second nucleic acid sequence using similarity default values for the amino acid residues encoded by the nucleic acid sequences. The default values include the following groups: (i) neutral/weakly hydrophobic residues which include the amino acid residues P, A, G, S and T; acidic/hydrophilic residues which include the amino acid residues Q, N, E, B, D and Z; basic/hydrophilic residues which include the amino acid residues H, K and R; hydrophobic/aliphatic residues which include the amino acid residues L, I, V and M; hydrophobic/aromatic residues which include the amino acid residues F, Y, and W; and C residues.

Preferred first D35E amino acid sequences of the present invention to use in the above methods include the D35E sequences identified herein as SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:31 or SEQ ID NO:32.

An organism category, as used herein, refers to the concept that a second D35E sequence as described herein is preferably a D35E sequence which is derived from an organism in the family, genus or species of the sequence being compared to such a D35E sequence (i.e., the first alignment). Selecting a sequence derived from a similar organism maximizes the ability to align such sequences. A preferred category from which the second D35E sequence is derived is the genus Herpes.

As used herein, randomization refers to the generation of a number of variations of an amino acid sequence by creating random spacial arrangements of amino acid residues within the initial residue and the terminal residue of said sequence by either insertion of spaces or deletion of amino acid residues. Positions in the amino acid sequence being randomized that represent non-conserved amino acids from a consensus sequence of the present invention, such as the D35E amino acid consensus sequence or the D35E amino acid sequence to which the randomizations will be aligned, are included in the randomizations as non-matching characters. Randomizations can also include substitutions of an amino acid residue or residues with ones having similar properties. Such default values for amino acid similarity are defined as amino acid residues which can be grouped as similar by the following properties: neutral/weakly hydrophobic: P, A, G, S, T; acidic/hydrophilic: Q, N, E, B, D, Z; basic/hydrophilic: H, K, R; hydrophobic/aliphatic L, I, V, M; hydrophobic/aromatic F, Y, W; cross-link forming C. Randomization can be generated manually, or preferably, by a computer. A preferred number of randomizations to be generated is at least 500; more preferably, 1000 randomizations would be generated; and even more preferably, 1500 randomizations would be generated. It is within the skill in the art to extrapolate the above discussion of randomizations to nucleic acid sequences.

As used herein, aligning refers to the act of bringing or arranging two amino acid or nucleic acid sequences into precise adjustment or correct relative position relative to each other, such that amino acid or nucleic acid identities or similarities, and position are maximized. Spacing of a consensus sequence to which the randomizations are compared is not altered. Preferably, an alignment would occur wherein the probability of two sequences aligning, at a given degree of alignment, with each other is not consistent with chance. More preferably, this probability would be p<0.05, and even more preferably, this probability would be p<0.01. Successful alignment, after accounting for changes by randomization in the spacing and default values of amino acid residues, is preferably greater than 40% with the consensus sequence, more preferably greater than 50%, more preferably greater than 60%, more preferably greater than 70%, more preferably greater than 80%, and most preferably greater than 90%.

As used herein, the term consensus sequence refers to an amino acid sequence, against which randomized sequences of the present invention can be aligned, which includes two or more amino acid residues and which is defined by the identity and relative positions of the amino acid residues. A preferred D35E consensus sequence for use in a method of the present invention include the D35E consensus sequence denoted herein as SEQ ID NO:1. With respect to amino acid sequences disclosed in the present invention, the use of "X" can refer to any single amino acid, no amino acid or more than one amino acid. Preferably, the use of "X" refers to any single amino acid.

As used herein, the term recombinogenic refers to the ability to catalyze or otherwise be involved with or effect recombination of nucleic acid molecules. Specifically, such recombination could include, but is not limited to DNA strand breakage and DNA strand transfer, and transposition of mobile elements.

The method of identifying whether a first amino acid sequence includes a recombinogenic sequence can further include a method of identifying an amino acid sequence which includes a site-specific DNA binding sequence associated with recombinogenic activity. This method further includes the steps of (e) isolating an amino acid sequence which is between about 1 and about 200 amino acid residues upstream of the carboxyl terminal end of the recombinogenic amino acid sequence identified in the first part of this method and (f) evaluating the amino acid sequence for the ability to bind to a nucleic acid sequence which includes a V(D)J recombination signal sequence or a V(D)J-like recombination signal sequence.

Similarly, the method of identifying whether a first nucleic acid sequence includes a recombinogenic sequence can further include a method of identifying an nucleic acid sequence which encodes an amino acid sequence which includes a site-specific DNA binding sequence associated with recombinogenic activity. This method further includes the steps of (e) isolating a nucleic acid sequence which is between about 1 and about 600 nucleic acid residues upstream of the carboxyl terminal end of the recombinogenic amino acid sequence encoded by the nucleic acid sequence identified in the first part of this method and (f) evaluating the amino acid sequence encoded by the nucleic acid sequence for the ability to bind to a nucleic acid sequence which includes a V(D)J recombination signal sequence or a V(D)J-like recombination signal sequence.

A search of the Herpes virus protein data base using various fragments of the D35E motif suggested that the Epstein-Barr gamma Herpes virus (EBV) BALF2 open reading frame contained a region which could be aligned readily with the D35E motif. While the BALF2 open reading frame has not been functionally characterized, this open reading frame is a member of the so called "major DNA binding- proteins" of Herpes viruses, which are known to be highly conserved among all members of the virus family. In particular, the protein ICP8 of Herpes simplex, an alpha type Herpes virus has been extensively characterized and is known to localize in the nucleus of infected cells during the lytic cycle of the virus, where it forms "replication compartments" required for completion of the viral lytic cycle.

Using the method to identify a recombinogenic motif of the present invention, the present inventors have identified a recombinogenic region of the Herpes virus DNA binding protein BALF2 and have discovered that this region of BALF2 is shared between Herpes simplex ICP8 (alpha Herpes virus) and reading frame 29 of VZV (beta Herpes virus), thus allowing functional comparisons between all members of this group, and reinforcing the highly conserved nature of the D35E motif in the Herpes virus family. Notably, in each case the D35E region is in a similar location in the mid-region of the molecule. In the case of ICP8, the DNA binding activity of the molecule has been localized to this region. Each D35E region is located approximately 100 amino acids towards the carboxyl terminus from another conserved motif, a putative zinc binding site. The site of this zinc-binding motif has been confirmed for ICP-8, and evidence presented herein also suggests functional zinc binding in BALF2.

The present inventors have also discovered that the V(D)J recombinase activating gene RAG-2 can also be aligned with the conserved D35E motif, although in this molecule the glutamate (E) residue of D35E is substituted by an aspartate (D) residue, a pattern also observed in the mariner and CpMar transposases. The location of this motif from RAG-2 is consistent with the localization of the RAG-2 DNA binding core. Remarkably, RAG-2 does not contain a zinc binding domain, but the related RAG-1 gene which synergises with RAG-2 does contain a zinc binding domain. Without being bound by theory, the present inventors believe that the close proximity of RAG-1 and RAG-2 in the genome suggests that at one point RAG-1 and RAG-2 were a single open reading frame similar to the Herpes major DNA binding protein containing both zinc binding and DNA binding domains. This open reading frame subsequently split into two co-regulated and synergistic open reading frames by a fortuitous rearrangement.

In vertebrates, expression of the RAG proteins has been identified as both necessary and sufficient to direct V(D)J recombination. Deletion of regions of RAG-1 and RAG-2 open reading frames (ORFs) similar to transcription activating regions of other proteins do not inactivate V(D)J recombination, suggesting that the RAG gene products are themselves responsible for V(D)J recombination, rather than inducers of other gene products. The present inventors have shown that both RAG proteins contain D35E like motifs which are particularly similar to the D35E motifs of retroviral integrases, a finding which may have important implications for retroviral pathogenesis.

These observations collectively have several implications. The presence of the D35E motif in the Herpes virus major DNA proteins suggests that these molecules collectively play a role in site-specific recombination of the Herpes virus genome, and can be modified to obtain Herpes virus species with altered replication properties for vaccines and other applications such as gene therapy. In support of the hypothesis that the major DNA binding proteins play a direct role in site-specific recombination, a monoclonal antibody directed against the extreme carboxyl terminus of BALF2 disrupts a complex termed TRBP (formed on EBV terminal sequences. This finding which suggests an antigenic relationship between BALF2 and factors which bind chi-like sequences similar to immunoglobulin class switch signals also implies a possible relationship between immunoglobulin class switching and the D35E motif.

In addition, the highly conserved D35E motif may be subject to pharmacological modulation, possibly yielding agents with activity against retroviral integrases such as that of the human immunodeficiency virus (HIV), and Herpes viruses, as well as immunomodulatory properties via interaction with RAG. Finally, since the site-specificity of DNA binding in the Tc transposases is separate from the D35E motif, via appropriate genetic engineering it may be possible to derive novel D35E based integrases with targeting to any defined sequence transcriptionally active in higher vertebrate organisms.

Another embodiment of the present invention relates to an isolated amino acid molecule which includes a first amino acid sequence. This first amino acid sequence can include a higher vertebrate amino acid sequence or a non-retroviral viral amino acid sequence. Such a first amino acid sequence has at least one identifying characteristic selected from the group of (a) two amino acid residues which include aspartate and glutamate, the residues being separated by at least about 30 amino acid residues; or (b) an ability to align with a second amino acid sequence which includes a D35E amino acid consensus sequence or a first D35E amino acid sequence. In a further embodiment, the first amino acid sequence aligns with a second D35E amino acid sequence in accordance with similarity default values selected from the groups of similarity default values as previously described herein. Another embodiment of the present invention relates to an isolated nucleic acid molecule which includes a nucleic acid sequence which encodes the first amino acid sequence described in this embodiment. Yet another embodiment of the present invention includes such a nucleic acid molecule which is operatively linked to an expression vector to form a recombinant molecule. Yet another embodiment relates to a recombinant cell which expresses such a recombinant molecule.

In further embodiments, the first amino acid sequence aligns with the second amino acid sequence with a probability not consistent with chance. In a preferred embodiment, such probability is p<0.05.

As used herein, the term "molecule" refers to a protein, amino acid sequence, a lipid, a nucleic acid sequence or an ion, and at times is used interchangeably with such terms. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably. Similarly, although the phrase "amino acid molecule" primarily refers to the physical amino acid molecule and the phrase "amino acid sequence" primarily refers to the sequence of amino acids on the amino acid molecule, the two phrases can be used interchangeably. In preferred embodiments, an isolated molecule of the present invention is derived from higher vertebrate and non-retroviral virus sequences. In another embodiment, such a molecule can include an amino acid sequence of a Herpes virus.

In other embodiments, the first D35E amino acid sequence includes, but is not limited to, the sequences denoted herein as SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:31 and SEQ ID NO:32. In another embodiment, the D35E consensus sequence is the sequence denoted as SEQ ID NO:1.

According to the present invention, the above-described isolated molecule can be further characterized as including a first amino acid sequence having the motif denoted herein as SEQ ID NO:2, which is a motif which the present inventors have determined defines a general motif for a recombinogenic amino acid sequence as described herein. In another embodiment, this motif has consensus residues denoted by underlining the particular consensus residues in the motif as follows: *N<u>XXXXXX</u>S<u>XXXWLKXXXXXXXXXXXXXXAXXGXLXAX</u>*. According to this embodiment, amino acid residues denoted by an asterisk "*" can be either an aspartate or a glutamate. Additionally, the first amino acid sequence has amino acid residues that are similar to at least about 6 of 11 of the underlined residues of the motif, wherein the similarity of the amino acid residues in the first amino acid sequence and the underlined residues in the motif is determined using similarity default values as previously described herein. It should be noted that the 6 of 11 residues in the first amino acid sequence are in approximately the same position as the 11 underlined residues in the motif.

As used herein, the term "motif" refers to a recurring, salient pattern which may be found in a given amino acid sequence or a nucleic acid sequence. For example, two different amino acid sequences may include a motif, such as that described above, because both sequences contain an identifiable, salient pattern of amino acid residues which has been defined as a motif. According to the present invention, the term "motif" can in some instances be used interchangeably with the term "sequence", in particular when referring to a sequence or sequences having a given motif, such as the recombinogenic motif described herein.

In further embodiments of the invention, the isolated molecule includes amino acid sequences that are substantially homologous to DNA binding proteins of Herpes viruses. In another embodiment, the isolated molecule is capable of regulating site-specific DNA recombination. According to the present invention, site-specific recombination can include DNA strand breakage, DNA strand transfer, and transposition of mobile elements. In yet another embodiment, the isolated molecule can be used to identify compounds which bind to the isolated molecule. Such molecules and their uses are described in detail below.

The present inventors have recently described in detail peptide fragments of the Herpes major DNA binding proteins and the vertebrate recombination activating genes (RAG) which share a common sequence motif known to direct site-specific recombination in invertebrate mobile DNA sequences and retroviruses. Evidence is provided herein which the present inventors believe indicates that the sequence motif contained in this region of these proteins is also involved in the class switching pathway of immunoglobulin genes.

In short, this approximately 34 to 39 amino acid sequence is a "master switch" for many recombination events of importance to both Herpes virus replication as well as the human immune response. Compounds which bind to the motifs described herein will be identified via binding to the motifs in vitro as an indication that they may inhibit the activity of the motif in vivo with pharmacological effects. Compounds can then be targeted to specific cell populations in vivo such as Herpes virus infected cells, T or B cells, or malignant cells via conjugation to monoclonal antibodies or liposomes binding to the desired cell. Such compounds and methods of delivery are discussed in detail below. Therefore, the use of this amino acid motif from Herpes virus and RAG will be of considerable importance in developing pharmaceutical compounds which for example inhibit Herpes virus replication without inhibiting class switching or V(D)J recombination, or which selectively inhibit V(D)J recombination or class switching for immunosuppression.

The identification of this functional motif in the Herpes virus major DNA binding proteins and RAG is novel and not predictable from the existing literature. Prior to the discovery herein, there is no known connection between the Herpes virus major DNA binding proteins and the RAG genes. There is also no localization of the recombinogenic regions of the major Herpes binding proteins or RAG to a particular peptide motif. Finally, there is also no reference to a possible functional relationship between either the Herpes major DNA binding proteins or RAG and the integrases of retroviruses such as HIV-1.

Also demonstrated for the first time herein is a site-specific DNA binding site which is shared between the Herpes major DNA binding proteins, the RAG proteins, and the integrases of retroviruses. These site-specific DNA binding sites exhibit specific binding to V(D)J and/or V(D)J-like recombination signals. While genetic evidence has suggested that a region of RAG-1 protein interacts with the sequences flanking the V(D)J recombination signal sequence (RSS), prior to the present invention, no V(D)J specific binding region of the RAG proteins has been identified or defined. Similarly, prior to the present invention, no V(D)J-like specific binding region of Herpes major DNA binding proteins or retroviral integrases has been identified or defined.

V(D)J recombination signal sequences (RSS) (i.e. used in immunoglobulin and T cell receptor rearrangement) are known in the art. Such RSSs are conserved sequences which consist of a block of seven nucleotides and a block of nine nucleotides separated by about 12 or about 23 base pair non-conserved DNA "spacers". These sequences are recognized by molecules which mediate recombination, and thus enable "site-specific" recombination in immunoglobulin genes or T cell receptor genes. A V(D)J-like RSS is a sequence derived from a different source than V(D)J RSS and has the characteristics and function of a V(D)J RSS.

As used herein, a site-specific DNA binding sequence associated with recombinogenic activity is an amino acid sequence which is capable of specifically binding to a V(D)J and/or a V(D)J-like RSS as described above. According to the present invention, such a DNA binding sequence includes at least one characteristic selected from the group of an association with recombinogenic activity, an ability to bind V(D)J and/or V(D)J-like recombination signal sequences, is located between about 1 and about 250 amino acids upstream of the carboxyl-terminal end of a recombinogenic amino acid sequence described herein (i.e. a sequence having a D35E-like motif), and is associated with a divalent cation binding region. In a preferred embodiment, a divalent cation binding region is a zinc binding region. Preferred site-specific DNA binding sequences of the present invention are RAG-1 site-specific DNA binding sequences, RAG-2 site-specific DNA binding sequences, Herpes major virus family site-specific DNA binding sequences and retroviral integrase site-specific DNA binding sequences. Most preferred site-specific DNA binding sequences of the present invention are the site-specific DNA binding sequences included in the recombinant molecules denoted pBA506/306 and pR2502/302. Such recombinant molecules are described in detail below. One embodiment of the present invention includes a recombinant molecule which has been modified such that said ability to bind V(D)J and V(D)J-like sequences is reduced.

In one embodiment of the present invention, a site-specific DNA binding sequence is an HIV integrase site-specific DNA binding sequence. Prior to the present invention, no HIV integrase site-specific DNA binding sequence had been identified. Characteristics of an HIV integrase site-specific DNA binding sequence include an association with recombinogenic activity, an ability to bind V(D)J and/or V(D)J-like recombination signal sequences, is located between about 1 and about 250 amino acids upstream of the carboxyl-terminal end of a recombinogenic amino acid sequence described herein (i.e. a sequence having a D35E-like motif), and is associated with a zinc binding region.

In one embodiment, a site-specific DNA binding sequence of the present invention is modified such that the ability of such sequence to bind to a V(D)J RSS and/or a V(D)J-like RSS is reduced. As used herein, the term "reduced" includes a measurable reduction in the ability to bind as well as total elimination of the ability to bind.

Another embodiment of the present invention relates to an isolated nucleic acid molecule which includes a nucleic acid sequence encoding a site-specific DNA binding sequence. The DNA binding sequence has at least one identifying characteristic which include (a) an association with recombinogenic activity; (b) an ability to bind V(D)J and V(D)J-like recombination signal sequences; (c) a location of between about 1 and about 200 amino acids upstream of the carboxyl-terminal end of a recombinogenic amino acid sequence that aligns substantially with a D35E amino acid consensus sequence; or (d) an association with a divalent cation binding region. In a further embodiment, the site-specific DNA binding sequence can include a RAG-1 site-specific DNA binding sequence, a RAG-2 site-specific DNA binding sequence, a Herpes virus site-specific DNA binding sequence, and a retroviral site-specific DNA binding sequence.

In another embodiment, such a nucleic acid sequence is operatively linked to an expression molecule to form a recombinant molecule. In another embodiment, such a recombinant molecule is expressed by a recombinant cell. In a preferred embodiment, a recombinant molecule including a nucleic acid sequence encoding a site-specific DNA binding site includes the recombinant molecules denoted herein as pBA501/304, pBA505/305, pBA506/306, pR2502/302 and pBA5001/3001.

One embodiment of the present invention relates to a recombinant cell that is preferably produced by transfecting a host cell with one or more recombinant molecules, each comprising one or more isolated nucleic acid molecules encoding proteins involved in a recombinogenic mechanism of the present invention. Such isolated nucleic acid molecules are operatively linked to an expression vector containing one or more transcription control sequences. The phrase operatively linked refers to insertion of a nucleic acid molecule into an expression vector in a manner such that the molecule is able to be expressed when transfected into a host cell. As used herein, an expression vector is a DNA or RNA vector that is capable of transfecting a host cell and of effecting expression of a specified nucleic acid molecule. Preferably, the expression vector is also capable of replicating within the host cell. Expression vectors can be either prokaryotic or eukaryotic, and are typically plasmids. Expression vectors of the present invention include any vectors that function (i.e., direct gene expression) in recombinant cells of the present invention, including in mammalian cells.

Transformation of a heterologous nucleic acid molecule (e.g., a heterologous recombinogenic amino acid sequence encoding nucleic acid molecule) into a cell suitable for use in the present invention can be accomplished by any method by which a gene is inserted into a cell. Transformation techniques include, but are not limited to, transfection, retroviral infection, electroporation, lipofection, bacterial transfer and spheroplast fusion. Nucleic acid molecules transformed into cells suitable for use in the present invention can either remain on extra-chromosomal vectors or can be integrated into the cell genome.

Expression of a nucleic acid molecule of the present invention in a cell can be accomplished using techniques known to those skilled in the art. Briefly, the nucleic acid molecule is inserted into an expression vector in such a manner that the nucleic acid molecule is operatively joined to a transcription control sequence in order to be capable of affecting either constitutive or regulated expression of the gene when the gene is transformed into a host cell. The phrase "recombinant molecule", as used herein refers to a gene operatively linked to at least one transcription control sequence on an expression vector. The phrase "expression vector", as used herein refers to a DNA or RNA vector that is capable of transforming a host cell, of replicating within the host cell, and of affecting expression of the operatively linked gene. Expression vectors are capable of replicating to either a high or low copy number depending on their inherent characteristics. Transcription control sequences, which can control the amount of protein produced, include sequences that control the initiation, elongation, and termination of transcription. Particularly important transcription control sequences are those which control transcription initiation, such as promoter and upstream activation sequences. Preferred host cells include, but are not limited to, a plant cell, an animal cell, a fungal cell, a yeast cell, a bacterial cell, an insect cell, an algal cell, an amoeboid cell and a protozoan cell.

An expression system can be constructed from any of the foregoing control elements operatively linked to nucleic acid sequences using methods known to those of skill in the art. See, for example, Sambrook et al., 1989, *Molecular Cloning: A Laboratory Manual*, Cold Spring Harbor Labs Press, which is incorporated by reference herein in its entirety.

Figure 3:
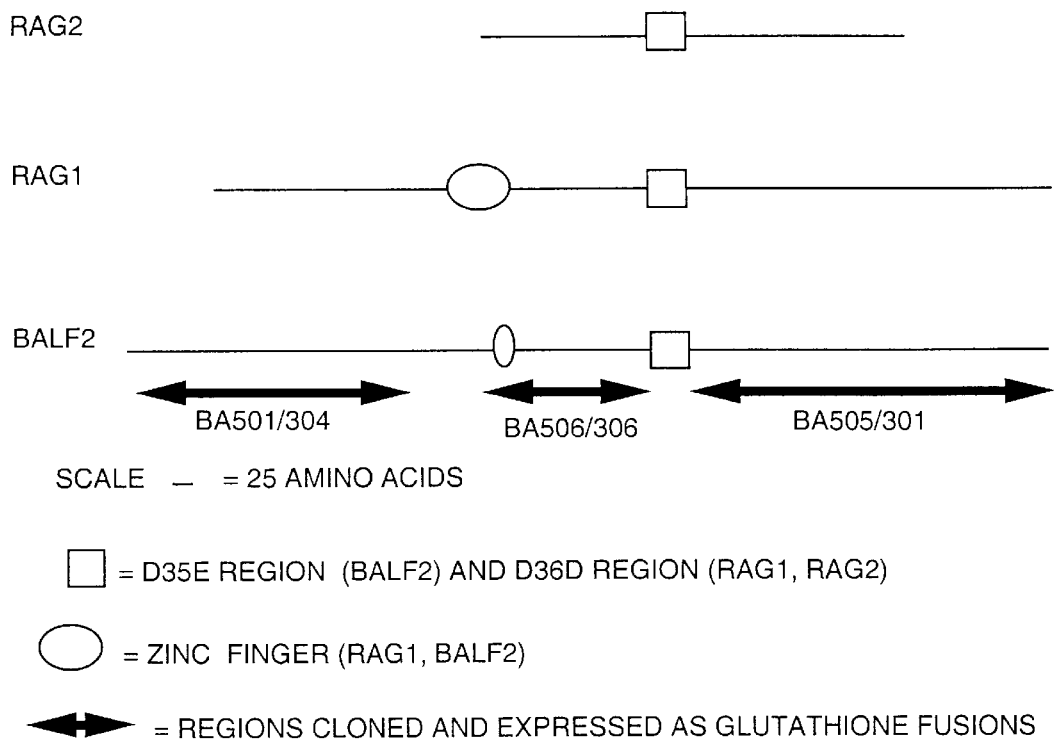
FIG. 3 is a schematic drawing illustrating the approximate position of recombinant molecules of the present invention with respect to the entire BALF2 protein.

A preferred recombinant molecule to be used in the present invention is a plasmid denoted pBA5001/3001, which comprises an entire open reading frame of a nucleic acid molecule which encodes an EBV BALF2 DNA binding protein (DBP) of the present invention. Such nucleic acid molecule is operatively linked to an expression vector. Other preferred recombinant molecules of the present invention include the plasmids denoted pBA506/306, pBA501/304 and pBA505/305, which comprise nucleic acid molecules encoding glutathione-binding protein fusion proteins which were generated from portions of the BALF2 protein, and are operatively linked to an expression vector. FIG. 3 illustrates the approximate position of the BALF2 portion of these proteins with respect to the entire BALF2 protein. Such a plasmid can be used to characterize DBP with altered recombination properties, or used in the in vitro assays described herein to identify a compound which binds to such protein, and in particular, to screen for compounds which inhibit both the EBV DBP and the RAG proteins, or which inhibit one protein but not the other. Another preferred recombinant molecule includes pR2502/302.

The term isolated nucleic acid molecule can include an isolated natural gene which encodes a protein involved in a protective cellular mechanism described herein, such as a protein involved in DNA repair, or a homologue thereof, which is described above. A nucleic acid molecule of the present invention can include one or more regulatory regions, full-length or partial coding regions, or combinations thereof. The minimal size of a nucleic acid molecule of the present invention is the minimal size that encodes for a protein which is involved in a protective cellular mechanism. It is to be noted that the term "a" or "an" entity refers to one or more of that entity; for example, an isolqted nucleic acid molecule refers to one or more isolated nucleic acid molecules or at least one nucleic acid molecule. As such, the terms "a" (or "an"), "one or more" and "at least one" can be used interchangeably herein. It is also to be noted that the terms "comprising", "including", and "having" can be used interchangeably.

An isolated nucleic acid molecule can also be produced using recombinant DNA technology (e.g., polymerase chain reaction (PCR) amplification, cloning) or chemical synthesis. Isolated nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode a protein which is involved in a protective cellular mechanism.

An isolated nucleic acid molecule of the present invention can include a nucleic acid sequence that encodes at least one protein described in the present invention. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably. Proteins of the present invention include, but are not limited to, proteins having full-length naturally occurring coding regions, proteins having partial coding regions, fusion proteins, and combinations thereof.

According to the present invention, an isolated, or biologically pure, protein, molecule or amino acid sequence is one that has been removed from its natural milieu. As such, "isolated" and "biologically pure" do not necessarily reflect the extent to which an entity has been purified. An isolated protein, molecule or amino acid sequence of the present invention can be obtained from its natural source, can be produced using recombinant DNA technology or can be produced by chemical synthesis. As used herein, a molecule of the present invention, such as a peptide or polypeptide, can be the full-length molecule or any homolog of such a molecule. Examples of such homologs include molecules in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homolog retains a desired activity of the natural molecule, such as, but not limited to, recombinogenic activity, and/or ability to elicit an immune response. These activities can be measured using techniques known to those skilled in the art.

Homologs can be the result of natural allelic variation or natural mutation. Homologs of the present invention can also be produced using techniques known in the art including, but not limited to, direct modifications to the protein or modifications to the gene encoding the protein using, for example, classic or recombinant DNA techniques to effect random or targeted mutagenesis.

The minimal size of a homolog of a peptide or polypeptide of the present invention is a size sufficient to be encoded by a nucleic acid molecule capable of forming a stable hybrid (i.e., hybridize under stringent hybridization conditions) with the complementary sequence of a nucleic acid molecule encoding the corresponding natural protein. As such, the size of the nucleic acid molecule encoding such a protein homolog is dependent on nucleic acid composition and percent homology between the nucleic acid molecule and complementary sequence. It should also be noted that the extent of homology required to form a stable hybrid can vary depending on whether the homologous sequences are interspersed throughout the nucleic acid molecules or are clustered (i.e., localized) in distinct regions on the nucleic acid molecules. The minimal size of such nucleic acid molecules is typically at least about 12 to about 15 nucleotides in length if the nucleic acid molecules are GC-rich and at least about 15 to about 17 bases in length if they are AT-rich. There is no limit, other than a practical limit, on the maximal size of such a nucleic acid molecule in that the nucleic acid molecule can include a portion of a gene, an entire gene, or multiple genes, or portions thereof. Similarly, the minimal size of a homolog of the present invention is from about 4 to about 6 amino acids in length, with preferred sizes depending on whether full-length, fusion, or other functional portions of such proteins are desired.

It should be noted that important aspects of the present invention include nucleic acid sequences which encode for amino acid sequences specifically disclosed herein and which encode for amino acid sequences which are identified by methods of the present invention. It is also to be noted that a double-stranded nucleic acid molecule of the present invention for which a nucleic acid sequence has been determined for one strand also comprises a complementary strand having a sequence that is a complement thereof. As such, nucleic acid molecules of the present invention, which can be either double-stranded or single-stranded, include those nucleic acid molecules that form stable hybrids under stringent hybridization conditions with either a given nucleic acid of the present invention. Methods to deduce a complementary sequence are known to those skilled in the art.

Another embodiment of the present invention is a recombinant virus, and preferably a Herpes virus, that is defective for reproduction in tissue culture. A reproduction defective virus is a virus that when inserted into an appropriate host cell is unable to form infectious virus due to modification of a recombinogenic portion of the viral genome.

The present invention includes a recombinant viral genome that includes a heterologous nucleic acid molecule that encodes a protective or therapeutic compound; the present invention also includes a recombinant virus containing such a genome. In a preferred embodiment, viruses of the present invention include non-retroviral viruses and more particularly include Herpes viruses. According to the present invention, a heterologous nucleic acid molecule that encodes a site-specific DNA binding site, or a portion thereof, can also include a recombinant retroviral viral genome. As used herein, a protective compound is a compound that when administered to an animal protects that animal from a disease corresponding to that compound. As used herein, the ability of a compound to protect an animal from a disease refers to the ability of that protective compound to treat, ameliorate and/or prevent the disease.

A protective compound of the present invention includes, but is not limited to, a protective protein and a protective RNA species. Essentially any heterologous nucleic acid molecule that encodes a protective protein or RNA can be used in the present invention. A protective protein of the present invention can be, for example, an immunogen that elicits an immune response which will protect an animal from the corresponding disease or some other compound (e.g., an immunomodulator, a toxin, an enzyme, an antibody, or other binding protein) that neutralizes and/or reduces the disease. A protective RNA of the present invention can be, for example, an RNA-based drug, a ribozyme, a molecule capable of triple helix formation, or an antisense RNA that effectively prevents the expression of a detrimental protein, thereby protecting an animal from disease.

It is within the scope of the present invention to produce therapeutic compositions against a variety of diseases, including infectious diseases, genetic diseases, and other metabolic diseases, including diseases that lead to abnormal cell growth, degenerative processes, and/or immunological defects. Therapeutic compositions of the present invention can protect animals from a variety of diseases including, but not limited to, allergies, autoimmune diseases, cancers, cardiovascular diseases, graft rejection, hematopoietic disorders, immunodeficiency diseases, immunoproliferative diseases, immunosuppressive disorders, infectious diseases, inflammatory diseases, jaundice, septic shock, other immunological defects, as well as other genetic or metabolic defects.

A preferred modified virus of the present invention includes a recombinant viral genome having a heterologous nucleic acid molecule encoding a protective compound that elicits an immune response. As used herein, a protective compound that elicits an immune response refers to a compound that when administered to an animal in an appropriate manner, known to those skilled in the art, leads to the production of an immune response in that animal against the protective compound. The immune response, which can include humoral and/or cell-mediated components, preferably protects the immunized animal against the disease(s) targeted by the protective compound. As such, preferred protective compounds include, but are not limited to, antigens associated with diseases, as disclosed herein.

Another preferred protective compound of the present invention is an immunomodulator. Suitable immunomodulators include compounds that enhance the immune response as well as compounds that suppress the immune response. Compounds that enhance the immune response include compounds that preferentially enhance humoral immunity as well as compounds that preferentially enhance cell-mediated immunity. Suitable compounds can be selected depending on the disease being targeted. Suitable immunomodulators include, but are not limited to, cytokines, chemokines, superantigens, and other immunomodulators as well as compounds that induce the production of cytokines, chemokines and other immunomodulators. Examples of such protective compounds include, but are not limited to, granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interferon gamma, interferon gamma inducing factor I (IGIF), transforming growth factor beta (TGF-β), RANTES (regulated upon activation, normal T-cell expressed and presumably secreted), macrophage inflammatory proteins (e.g., MIP-1 alpha and MIP-1 beta), and Leishmania elongation initiating factor (LEIF).

One preferred embodiment of the present invention is a recombinant virus having more than one heterologous nucleic acid molecule included in the viral genome. Such a virus can include two or more heterologous nucleic acid molecules encoding two or more protective compounds to protect an animal from a given disease, or can include two or more heterologous nucleic acid molecules encoding protective compounds each targeted against a different disease. A preferred multivalent virus can also include an heterologous nucleic acid molecule encoding a protective compound that elicits an immune response as well as an heterologous nucleic acid molecule encoding an immunomodulator to enhance the desired immune response. Also included in the present invention are protective compounds that are fusion, or multivalent, proteins comprising more than one functional domain.

One aspect of the present invention includes a method to identify compounds that bind to recombinogenic motifs described herein or identified by the methods described herein. Another aspect includes a method to identify compounds that regulate recombinogenic sequences as described herein. Such compounds are referred to herein as "putative regulatory compounds". More particularly, one embodiment of the present invention includes a method to identify a compound that binds to a recombinogenic amino acid sequence as described herein or to a site-specific DNA binding sequence as described herein. Such sequences include amino acid sequences encoded by a nucleic acid sequence as set forth herein and the nucleic acid sequences, as well as sequences identified by any of the methods set forth herein. Such a method of identifying a compound can include, for example, (a) contacting a putative binding compound with the amino acid sequence; and (b) detecting binding of the putative binding compound to the amino acid sequence.

As used herein, the term "putative" refers to compounds having an unknown binding and/or regulatory activity, at least with respect to the ability of such compounds to bind to recombinogenic molecules and effect recombination events associated with such molecules. Putative binding and/or regulatory compounds as referred to herein include, for example, compounds that are products of rational drug design, natural products and compounds having partially defined signal transduction regulatory properties. A putative compound can be a protein-based compound, a carbohydrate-based compound, a lipid-based compound, a nucleic acid-based compound, a natural organic compound, a synthetically derived organic compound, a monoclonal antibody, an anti-idiotypic antibody and/or catalytic antibody, or fragments thereof. A putative binding and/or regulatory compound can be obtained, for example, from molecular diversity strategies (a combination of related strategies allowing the rapid construction of large, chemically diverse molecule libraries), libraries of natural or synthetic compounds, in particular from chemical or combinatorial libraries (i.e., libraries of compounds that differ in sequence or size but that have the same building blocks) or by rational drug design. See for example, Maulik et al., 1997, *Molecular Biotechnology: Therapeutic Applications and Strategies*, Wiley-Liss, Inc., which is incorporated herein by reference in its entirety.

In a molecular diversity strategy, large compound libraries are synthesized, for example, from peptides, oligonucleotides, carbohydrates and/or synthetic organic molecules, using biological, enzymatic and/or chemical approaches. The critical parameters in developing a molecular diversity strategy include subunit diversity, molecular size, and library diversity. The general goal of screening such libraries is to utilize sequential application of combinatorial selection to obtain high-affinity ligands against a desired target, and then optimize the lead molecules by either random or directed design strategies. Methods of molecular diversity are described in detail in Maulik, et al., ibid.

In a rational drug design procedure, the three-dimensional structure of a regulatory compound can be analyzed by, for example, nuclear magnetic resonance (NMR) or X-ray crystallography. This three-dimensional structure can then be used to predict structures of potential compounds, such as putative regulatory compounds by, for example, computer modeling. The predicted compound structure can be used to optimize lead compounds derived, for example, by molecular diversity methods. In addition, the predicted compound structure can be produced by, for example, chemical synthesis, recombinant DNA technology, or by isolating a mimetope from a natural source (e.g., plants, animals, bacteria and fungi).

Using the binding assays described below in this disclosure compounds which bound to only the Herpes virus motifs but not the RAG motif would be predicted to have anti-Herpes virus activity without immunosuppressive effects. Similarly, compounds which bound only to the RAG motif would be predicted to be specific for suppression of V(D)J recombination. Compounds which bind to the BALF2 motif would also be predicted to have possible effects upon the process of immunoglobulin class switching pathway since the present inventors have presented evidence herein that the BALF2 protein is related to the as yet unidentified recombinase utilized in immunoglobulin class switching. It is also worth noting that the motifs described herein are also shared with retroviral integrases, and thus compounds which are identified as binding to these motifs may also have in vivo activity against retroviruses such as the human immunodeficiency virus (HIV) via inhibition of the HIV integrase.

One embodiment of the present invention includes antibodies capable of selectively binding to a recombinogenic amino acid sequence or a site-specific DNA binding sequence as described herein or to a sequence identified by any of the methods described herein. Such an antibody is useful in the clinical detection of functional viral replication proteins and in the detection of recombinase gene products. As used herein, the term "selectively binds to" refers to the ability of such an antibody to preferentially bind to such sequences and mimetopes thereof. Antibodies of the present invention can be either polyclonal or monoclonal antibodies. Antibodies of the present invention include functional equivalents such as antibody fragments and genetically-engineered antibodies, including single chain antibodies, that are capable of selectively binding to at least one of the epitopes of the protein or mimetope used to obtain the antibodies. Antibodies of the present invention can include chimeric antibodies in which at least a portion of the heavy chain and/or light chain of an antibody is replaced with a corresponding portion from a different antibody. For example, a chimeric antibody of the present invention can include an antibody having an altered heavy chain constant region (e.g., altered isotype), an antibody having protein sequences derived from two or more different species of animal, and an antibody having altered heavy and/or light chain variable regions (e.g., altered affinity or specificity). Preferred antibodies are raised in response to the amino acid sequences or mimetopes thereof described herein.

Generally, in the production of an antibody, a suitable experimental animal, such as a rabbit, hamster, guinea pig or mouse, is exposed to an antigen against which an antibody is desired. Typically, an animal is immunized with an effective amount of antigen that is injected into the animal. An effective amount of antigen refers to an amount needed to induce antibody production by the animal. The animal's immune system is then allowed to respond over a predetermined period of time. The immunization process can be repeated until the immune system is found to be producing antibodies to the antigen. In order to obtain polyclonal antibodies specific for the antigen, serum is collected from the animal that contains the desired antibodies. Such serum is useful as a reagent. Polyclonal antibodies can be further purified from the serum by, for example, treating the serum with ammonium sulfate. In order to obtain monoclonal antibodies, the immunized animal is sacrificed and B lymphocytes are recovered from the spleen. The B lymphocytes are then fused with myeloma cells to obtain a population of hybridoma cells capable of continual growth in suitable culture medium. Hybridomas producing a desired antibody are selected by testing the ability of an antibody produced by a hybridoma to bind to the antigen.

A preferred method to produce antibodies of the present invention includes administering to an animal an effective amount of an amino acid sequence described herein or mimetope thereof to produce antibodies thereto and recovering such antibodies. Preferred proteins for administration to an animal include, but are not limited to, recombinogenic amino acid sequences, site-specific DNA sequences and/or mimetopes thereof. Preferred proteins for producing antibodies include recombinogenic amino acid sequences, site-specific DNA sequences and fusion proteins made with such sequences. More preferred proteins includes a peptide having the amino acid sequence denoted herein as SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:31 or SEQ ID NO:32, or the amino acid sequences included in the plasmids denoted herein as pBA501/304, pBA505/305, pBA506/306, pR2502/302 or pBA5001/3001. Preferred monoclonal antibodies of the present invention have the isotype IgG1, IgG2a, IgG2b, IgA or IgM.

Another embodiment of the present invention includes an antibody that specifically binds to the idiotype of the antibody described above. Such antibodies are referred to herein as anti-idiotype antibodies and are known in the art. For example, monoclonal antibodies generated which bind to a recombinogenic motif or sequence can be used to generate anti-idiotype antibodies. These anti-idiotype antibodies could also be used directly as therapeutic agents since they would bind to and inhibit endogenous factors which bind to the motif. Monoclonal antibodies which bind to the motif could also be used in RIA for clinical detection of functional Herpes virus replication protein, or presence of the RAG gene product. Anti-idiotype antibodies can be used in any of the methods, assays or kits described herein for an antibody or compound.

In one embodiment of the present invention, antibodies described herein can be used in a test kit for testing for the presence of a virus having a recombinogenic amino acid sequence. Such a test kit can include the antibody and a means for determining an immunoreaction between the antibody and a recombinogenic amino acid sequence in an assay. Means for determining immunoreactions can be any means for determining an immunoreaction, such as an ELISA, FACS analysis, or Western blot. Such methods are described in detail below.

Another embodiment of the present invention includes an antibody as described above, wherein the antibody binds to a viral recombinogenic amino acid sequence. Such an antibody can be used to diagnose a viral infection. Such a method includes the steps of (a) contacting a serum sample from an animal with the antibody; and (b) detecting the binding of the antibody to the viral recombinogenic amino acid sequence.

An assay based upon ELISA technology could be devised as follows: (1) biotinylated peptides containing the motifs described herein could be synthesized; (2) the compound of interest could be immobilized in a microliter well; (3) the biotinylated peptides could be incubated in solution in the wells; (4) bound peptide could be assayed by development of the assay with anti-biotin secondary antibody conjugated to alkaline phosphatase (AP) or horse radish peroxidase (HRP) and the assays could be assessed for positive binding via an automated optical density reader.

A simple Radio Immuno Assay (RIA) based screen for pharmaceutical compounds which bind to this motif could be devised as follows: (1) monoclonal antibodies against the peptide motifs identified herein could be generated; (2) peptide fragments of the motif could be synthesized in vitro and immobilized to micro titer wells; (3) antibodies could be radioactively labeled and bound to the immobilized motif; (4) compounds would be screened for binding via displacement of the labeled antibody into the media which could be monitored via an automated radioactivity counter.

In yet another assay, a recombinogenic or site-specific DNA binding amino acid sequence is contacted with a putative binding compound. During the step of contacting, the sequence is initially complexed to an antibody that specifically recognizes the amino acid sequence. The method further comprises detecting displacement of the antibody from the amino acid sequence by the putative binding compound.

Yet another embodiment of the present invention includes a method to regulate site-specific recombination in an organism. Such a method includes the steps of administering to an organism a composition comprising an appropriate delivery vehicle and an effective dose of a compound. Such a compound can include a compound that binds to an isolated recombinogenic molecule as set forth herein or to an antibody. Sush an antibody can include an antibody that specifically binds the isolated molecule or an antibody that specifically recognizes the idiotype of the first antibody. This compound preferably has the effect of regulating site-specific recombination in the organism. Preferably, such an organism is a higher vertebrate or a virus. In one embodiment, the step of regulating comprises suppressing site-specific recombination. Such a method can be used, for example, to regulate site-specific recombination in cells which include, but are not limited to, B lymphocytes, T lymphocytes, and malignant cells.

The methods to regulate site-specific recombination as described herein are particularly useful to regulate immunoglobulin class switching, to regulate virus activity, to regulate virus-induced autoimmune disease, to regulate lymphoproliferative diseases and to stimulate growth and development of hematopoietic cells. In particular, such methods are useful to regulate herpes virus activity and to regulate retrovirus activity, particularly human immunodeficiency virus activity. A particular advantage of such methods is that the method can be designed to avoid regulating normal site-specific recombination by recombinase activating genes, while regulating one of the above-described activities.

As used herein, "an effective amount" of such a compound is an amount, or dose, of a regulatory compound, that when administered to an organism, is capable of regulating site-specific recombination in the organism.

Effective doses to administer to an organism include doses administered over time that are capable of regulating site-specific recombination in the organism. For example, a first effective dose can comprise an amount of a regulatory compound of the present invention that causes a minimal change in site-specific recombination when administered to an organism. A second effective dose can comprise a greater amount of the same compound than the first dose. Effective doses can comprise increasing concentrations of the compound necessary to regulate site-specific recombination and ameliorate a disease involving such site-specific recombination in an organism such that the organism does not have an immune response to subsequent exposure to the compound. A suitable single dose of a regulatory compound of the present invention is a dose that is capable of substantially regulating site-specific recombination when administered one or more times over a suitable time period. A preferred single dose of a regulatory compound ranges from about 0.01 µg to about 1,000 milligrams (mg) of such a compound per subject, more preferred ranges being from about 0.1 µg to about 100 mg of a compound per subject, and even more preferred ranges being from about 1 µg to about 10 mg of a compound per subject.

A regulatory compound of the present invention can be administered to any organism, preferably to animals, and more preferably to mammals, and even more preferably to humans. Acceptable protocols to administer a regulatory compound of the present invention in an effective manner include individual dose size, number of doses, frequency of dose administration, and mode of administration. Determination of such protocols can be accomplished by those skilled in the art depending upon a variety of variables, including the animal to be treated and the stage of disease. Modes of delivery can include any method compatible with prophylactic or treatment of a disease. Modes of delivery include, but are not limited to, parenteral, oral, intravenous, topical administration, local administration, and ex vivo administration to isolated cells.

Yet another embodiment of the present invention relates to a therapeutic composition used to regulate site-specific recombination in an organism. Such a therapeutic composition can include a compound selected from the group of a compound that binds to an isolated recombinogenic molecule or a site-specific DNA binding molecule as set forth in herein or an antibody. Such an antibody can include a first antibody that specifically binds to the isolated recombinogenic molecule or a second antibody that specifically recognizes the idiotype of the first antibody.

In another embodiment, a therapeutic composition of the present invention includes a vector derived from a virus having a recombinogenic nucleic acid sequence which encodes a recombinogenic molecule as set forth herein. The recombinogenic nucleic acid sequence has been modified such that circularization of the vector is irreversible. The therapeutic composition also includes a nucleic acid molecule encoding a therapeutic compound to be expressed in an organism, such a nucleic acid molecule being operatively linked to the modified vector. A therapeutic compound can be used for gene therapy, for example.

Yet another embodiment of the present invention relates to a vaccine comprising an isolated virus derived from a virus having a recombinogenic nucleic acid sequence encoding a recombinogenic amino acid sequence as set forth herein. In this vaccine, the recombinogenic nucleic acid sequence has been modified to be non-recombinogenic.

In one embodiment of the present invention, a binding compound, a regulatory compound, a therapeutic composition, a vaccine, or a viral vector are administered to an organism with a delivery vehicle, or a pharmaceutically acceptable carrier. Such carriers can include a heterologous compound which is used for targeting. Such heterologous compounds include, but are not limited to an antigen, a drug, a marker, an antibody, a cytokine, a hormone, a growth factor, proteins, peptides, toxins, microbial agents, or inert particles.

As used herein, a "pharmaceutically acceptable carrier" refers to any substance suitable as a vehicle for delivering a compound, composition, vaccine or vector of the present invention to a suitable in vitro or in vivo site of action. Such a carrier is preferably able to deliver the regulatory compound to cells undergoing site-specific recombination, and more preferably to a particular site, in an organism. Preferred carriers are capable of maintaining regulatory compounds of the present invention in a form that is capable of regulating site-specific recombination in a cell. Examples of such carriers include, but are not limited to water, phosphate buffered saline, Ringer's solution, dextrose solution, serum-containing solutions, Hank's solution and other aqueous physiologically balanced solutions. Aqueous carriers can also contain suitable auxiliary substances required to approximate the physiological conditions of the recipient, for example, by enhancing chemical stability and isotonicity. Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- and o-cresol, formalin and benzol alcohol. Preferred auxiliary substances for aerosol delivery include surfactant substances non-toxic to a recipient, for example, esters or partial esters of fatty acids containing from about six to about twenty-two carbon atoms. Examples of esters include, caproic, octanoic, lauric, palmitic, stearic, linoleic, linolenic, olesteric, and oleic acids. Formulations of the present invention can be sterilized by conventional methods and/or lyophilized.

Useful carriers for compounds, compositions, vectors or vaccines of the present invention include any artificial or natural lipid-containing target molecule, preferably cells, cellular membranes, liposomes, and micelles. Preferably, formulations of the present invention are administered in the form of liposomes or micelles. Liposome and micelles of the present invention are capable of delivering a regulatory compound from the extracellular space of a cell to the intracellular space of a cell. Concentrations of a regulatory compound of the present invention combined with a liposome or a micelle include concentrations effective for delivering a sufficient amount of compounds of the present invention to a cell such that regulation of site-specific recombination is effected. Such delivery systems are known and have been successfully applied in the art and are discussed in Maulik et al., ibid., which is incorporated by reference herein in its entirety.

Another embodiment of the present invention relates to a method to produce a vector for production of a therapeutic composition. Such a method includes the steps of modifying a recombinogenic nucleic acid sequence of a virus to make the virus non-recombinogenic. The recomrinogenic nucleic acid sequence encodes an isolated molecule as set forth herein. The step of modifying can be accomplished by producing irreversible circularization of the virus using a method which includes (a) selectively deleting the recombinogenic nucleic acid sequence upon circularization of the virus and (b) selectively mutating the recombinogenic nucleic acid sequence. The step of mutating can be accomplished by adding nucleic acids, deleting nucleic acids or substituting nucleic acids. This method of producing a vector further includes the step of introducing a nucleic acid molecule encoding a therapeutic compound into the virus.

EBV infection of primary B cells and B cell lines has been associated with increased expression of the recombination activating genes (RAG-1 and RAG-2) required for the initiation of immunoglobulin gene V(D)J recombination in B cells. The novel findings disclosed in the present invention indicate that EBV and other herpes viruses may utilize a pathway co-regulated and possibly similar to the process of immunoglobulin and T cell receptor gene recombination for the transition from the linear to the episomal genomic configuration. EBV infection of the T lymphoblastic cell line HPB-ALL also partially blocks the down-regulation of RAG expression via cross-linking of the T-cell receptor, suggesting that EBV infection of T-cells may directly alter the T cell receptor repertoire. It is one embodiment of the present invention to identify compounds which bind to D35E sequences which interfere with both herpes virus circularization and linearization. Such compounds are of therapeutic value in the treatment of herpes virus infection. Similarly, it is an embodiment of the present invention to identify compounds which bind to these regions of the RAG proteins which interfere with the process of immunoglobulin and T cell receptor gene recombination, which is also of therapeutic value as immunomodulatory agents.

The previously unappreciated similarities between the DBP and RAG proteins and the D35E recombinase superfamily have important implications for viral infection related auto-immunity and pathogenesis. Defining and altering a shared pathway between viral and cellular recombination activating genes in order to generate non-recombinogenic and non-pathogenic Herpes virus strains useful in gene therapy and/or Herpes virus vaccination is one embodiment of the present invention.

The following examples are provided for the purposes of illustration and are not intended to limit the scope of the present invention.

EXAMPLES

Example 1

The following example shows the use of the method to identify recombinogenic amino acid sequences of the present invention to identify several recombinogenic amino acid sequences.

V(D)J-like regions of the tandemly repeated Epstein Barr virus (EBV) NJHET sequence were identified by manual alignment with the termini of Tc elements and V(D)J recombination signals using consensus regions identified by the present inventors (data not shown). A sequence termed EBV was found most similar to known V(D)J signals by several criteria including the presence of a heptamer-like and nonamer-like regions in correct orientation, as well as the conservation of this sequence in each NJHet repeat (data not shown). Deletion breakpoints of the Raji cell deletion within the Herpes virus DNA binding protein, BALF2, open reading frame (ORF) were determined via direct sequence analysis of the Raji cell DNA and comparison to the B958 DNA in this region (data not shown).

The EV(D)J sequences are present as a single copy in each of the NJhet terminal repeats. Since each NJhet repeat is present in a multiple tandemly duplicated array, this tandem array of V(D)J-like sequences could provide both a mechanism for circularization of the genome through head to head joining of the V(D)J like regions, as well as regeneration of the NJhet region via head to tail joining of the V(D)J like regions. In support of the possibility that V(D)J like sequences may define sites of EBV recombination in vivo, the present inventors note that the termini of a deletion in the BALF2 ORF which appear to render the virus trapped in the episomal state are similar to the termini of immunoglobulin RSS. Since the Raji episome cannot enter a lytic replication cycle due to the absence of functional BALF2 protein, it seems likely that this deletion occurred during the initial transition of the virus from the linear to the circular episomal state. Thus, excision of DNA sequences between V(D)J like RSS may provide a mechanism for recombination of internal as well as terminal EBV sequences.

After the identification of V(D)J RSS like sequences in the termini of EBV and flanking in vivo EBV genomic deletions, the present inventors searched for a site-specific recombinase encoded by EBV and related Herpes viruses. As noted above, a widely distributed motif denoted "D35E" functions as a catalytic center for strand exchange in both invertebrate transposases and retroviral integrases. Using a search strategy targeted to the EBV genome and a D35E consensus sequence generated from invertebrate Tc and prokaryotic IS elements the present inventors identified a D35E-like region within the EBV BALF2 protein. Properties of the BALF2 protein were consistent with a role of this protein as a viral recombinase.

Amino acid sequences of all EBV ORF were searched for sequences similar to conserved portions of the D35E motif using the Macvector sequence analysis package. Default values for amino acid similarity from the Macvector package are as follows: neutral/weakly hydrophobic: P, A, G, S, T; acidic/hydrophilic: Q, N, E, B, D, Z; basic/hydrophilic: H, K, R; hydrophobic/aliphatic L, I, V, M; hydrophobic/aromatic F, Y, W; cross-link forming C. The sequence most similar to the D35E amino terminus in the EBV data base was identified within the BALF2 open reading frame as shown in Table 1A. Table 1A is an alignment of the BALF2 sequence (SEQ ID NO:5) and a D35E Tc sequence, Tc/IS3 (SEQ ID NO:3).

The present inventors also discovered that these D and E residues and D35E like regions are present in other DBP, suggesting a possible conservation of function. Using the BALF2 protein sequence as a pattern, D35E-like regions were also identified in all other DBP available for analysis including Herpes simplex (ICP8 protein aa 547–580), Varicella zoster (VZV29 protein aa 543–577), human Cytomegalovirus (DBP aa 671–710), murine Cytomegalovirus (DBP aa 685722), Herpes saimiri (DBP aa 640–678), equine Herpes virus (DBP aa 649–686), and human Herpes virus 6 (DBP aa 654–699). The BLAST protein homology search was used to identify D35E-like regions of Herpes DNA binding proteins (DBP) closely related to EBV, while less closely related D35E-like regions of the Herpes simplex ICP8 and Varicella zoster VZV29 proteins were identified via the search method described below for identification of D35E-like regions in the RAG proteins. Table 1B shows a comparison of the BALF2 recombinogenic sequence SEQ ID NO:5 with the identified recombinogenic sequences from other Herpes DBPs, equine Herpes virus (EH2, SEQ ID NO:6), murine cytomegalovirus (mCMV, SEQ ID NO:7) human Herpes virus 6 (HH6, SEQ ID NO:8), Herpes saimiri (HSa, SEQ ID NO:31) and human cytomegalovirus (hCMV, SEQ ID NO:32). Table 1C shows a comparison of the BALF2 recombinogenic sequence SEQ ID NO:5 with the identified recombinogenic sequences from ICP8 (SEQ ID NO:10) and VZV29 (SEQ ID NO:9), and the comparison of these sequences with each other.

Example 2

The following example illustrates the identification of D35E-like recombinogenic sequences in the RAG genes.

The present investigators determined whether EBV mediated recombination at V(D)J RSS like sequences occurred via the vertebrate RAG proteins required for recombination of immunoglobulin and T cell receptor genes, rather than via a virally encoded protein. Catalytic D35E-like motifs might also be present in the RAG proteins required for recombination of the immunoglobulin and T cell receptor genes. D35E-like motifs identified in the vertebrate recombination

TABLE 1

```
A.)
BALF2       ENDNPGLGQSPPEWLKGHYQTLCTNFRSLAIDKGVLTAKE
aa 640      :|     :     |||            :       | : |
Tc/IS3      DN   H SRK R WLK        KV LL  PS SPDLNPIE

B.)
BALF2       DNPGLGQSPPEWLKGHYQTLCTNFRSLAIDKGVLTAKE
aa 640      :||::| ||:|||| ||||| |||:   ||||||||: |
EH2         ENPAVGVSPGEWLKMHYQTLWTNFKNSCIDKGVLTGTE
aa 649

BALF2       DNPGLGQSPPEWLKGHYQTLCTNFRSLAIDKGVLTAKE
aa 640      |||   :   : |:  |:|::|:  | : :: || |  |:
MCMV        DNPLTTAQISAWVTLHFQSICGAFGTTPLKKGFLNVKD

BALF2       DNPGLGQSPPEWLKGHYQTLCTNFRSLAIDKGVL  T     A   KE
aa 640      |  | |:| :  |   ||:| : |:|  : ||  |     |   :
HH6         DRPCTGNSISKVLVQQYQSLYGTFHSSYLKKGFLNTRTVKVASNVD
aa 654

C.)
BALF2       DNPGLGQSPPEWL K GHYQTLCTNFRSLAIDKGVLTAKE
aa 640      |  |   :     ||| |    :   ::   | : :: |
VZV29       DPLGNYAP YLILRKPGD QTEAAK ATMQ D TYRATLE
aa 543

BALF2       DNPGLGQSPPEWLKGHYQTLCTNFRSLAIDKGVLTAKE
aa 640      |  |   : :  ||    :   |   |::  :    :| |
ICP8        DVLGNYAAFSA LKRAD GSETA RTIMQE TYRAATE
aa 547

VZV29       DPLGNYAPYLILRKPGD  QTEAAKATMQDTYRATLE
aa 543      | ||||||::  | |   |   :         ||:||||:||
ICP8        DVLGNYAAFSAL KRADGSET ARTI MQETYRAATE
aa 547
```

The BALF2 D35E-like motif defines a subgroup of motifs closely shared with Cytomegalovirus, Herpes saimiri, human Herpes virus 6, and equine Herpes virus D35E-like regions of ICP8 and VZV29 define a second subgroup of motifs. All D35E-like regions are located in the mid-portion of the DBP, each of which is approximately 1000 to 1100 amino acids in size (initial amino acid of the respective motifs ranging from amino acid 543 in Varicella zoster virus to amino acid 685 in murine Cytomegalovirus). In the case of ICP8, the conserved D35E-like region is located within an experimentally determined non-specific DNA binding site of the ICP8 molecule. Some motifs such as those of Cytomegalovirus (human and murine, human not shown) and human Herpes virus 6 have a D-spacer-D pattern, while equine Herpes virus has an E-spacer-E pattern, similar to substitution of D and E residues in the D35E sequences of invertebrate transposases. Alignment of EBV (BALF2) and human Herpes virus 6 motifs (Table 1) also suggests that the carboxyl-terminus of the motif may be more variable than the amino-terminus, since a block of 5 unaligned amino acids is present in the human Herpes virus 6 carboxyl-terminus not present in other motifs.

activating gene (RAG) proteins most closely match a consensus of D35E motifs including the retroviral integrases.

A novel search strategy was used to identify D35E-like regions in the RAG proteins. To identify D35E like regions of the RAG proteins, all conserved D (aspartate) residues within the functional core of the RAG-2 ORF which contained a D (aspartate) or E (glutamate) residue 34 to 39 amino acids from the initial D (D/DE regions) were identified using a consensus sequence from sequenced RAG-2 genes. The internal amino acids of candidate D/DE regions of the RAG-2 ORF were then aligned with the internal amino acids of the D35E consensus of mobile sequences and retroviral integrases denoted IS3/RP (SEQ ID NO:4). This revealed a motif shown in a 38 amino acid sequence initiating at residue 202 of the RAG-2 ORF (SEQ ID NO:12) as a possible match to the D35E consensus based upon similarity of internal residues to the IS3/RP consensus.

The probability of obtaining the a specified number of aligned internal sequences between the RAG-2 sequence and the motif consensus was then estimated by generating a distribution of 1500 randomized RAG-2 internal sequences, and identifying the percentile corresponding to the observed number of aligned residues. The initial and terminal residues of the RAG-2 motif, and the IS3/RP D35E motif were not used in this analysis, since these matches were forced due to the nature of their identification. Spacing of the D35E motif was not altered, and spaces representing non-conserved amino acids from the D35E motif were included in the randomizations as non-matching characters. Probability values of less than 0.001 were obtained that the observed alignments between the RAG-2 internal sequence and the D35E motif were the result of chance either for amino acid identity or similarity. A sequence in the RAG-1 ORF (SEQ ID NO:11)was subsequently identified by its similarity to the RAG-2 motif (p<0.01, data not shown).

Table 2 shows the comparison of the D35E consensus sequence, SEQ ID NO:4, and the identified recombinogenic sequences in the RAG1 (SEQ ID NO:11) and the RAG2 (SEQ ID NO:12) genes. Alignment between RAG-2 and RAG-1 D35E-like regions was also significant (P<0.01). Both human and murine RAG-1 sequences are essentially identical in this region of the RAG-1 proteins, which is within the functional core of the molecule required for V(D)J recombination. Similarly, the RAG-2 proteins from a variety of vertebrate species are also essentially identical in this region of the RAG-2 protein.

TABLE 2

```
mRAG2   DGLSFHVSIARNDTVYILGGHSLANNIRPANLYRIRVD
aa 202  | | | |                    |   :::|  |  :
IS3/4P  DN S H SR  R  Q     I  L  P YSPQLN I EE
        | | |                      :       |  : |:
mRAG1   DGLSGLASSVDEYPVDTIAKRFRYDSALVSALMDMEED
aa 537
```

Comparison of the RAG D35E regions to D35E regions of invertebrate transposons and retroviral integrases showed that RAG-2 in particular shared many amino acid residues with the retroviral integrases. Table 3 shows the comparison between the RAG2 recombinogenic sequence (SEQ ID NO:12) and murine leukemia virus (MMLV, SEQ ID NO: 13) and D. melanogaster mobile (Copia, SEQ ID NO:14). A consensus sequence between the RAG2 recombinogenic sequence (SEQ ID NO:12) and one or both retroviral integrases is denoted R/I (SEQ ID NO:15). In addition, Table 3 shows the comparison between the human immunodeficiency virus integrase D35E motif (SEQ ID NO:16) and human RAG2 (SEQ ID NO:12).

TABLE 3

```
A.)
MMLV    DNGPAF VSKVS Q TVADLLGIDWK LHCAYRP QS SGQV E
        |  |  :| || :: :  ||    | |    : |    || :     | :
RAG2    D GLSFHVS IARNDTVYILGG   HSLANNIRPANLYRIRV D
        | |   :|  |: |     |    | |:    | :|    | :
CopiaDNGR EYLSNEMRQFCVKK  GISYH LTVPHTP QL NG VSE

R/I     D G  F VS   RQ TV  L G   H L    RP QL    V E

B.)
hRAG2D  GLS FHVSIA KNDTIYILGGHSLANNIRPAN LYRIRVD
        | | | |  | | |  : : | :     | | |      |:
HIV1    DNG SNFT SAAVK AACWWAGIKQEFG I PYNPQSQGVVE
```

The present inventors have identified sequences within the termini of EBV which appear similar to both the termini of invertebrate mobile DNA sequences and V(D)J RSS and shown that these sequences might provide a recognition signal for EBV circularization via a pathway analogous to the transposition of mobile DNA sequences and the recombination of immunoglobulin and T cell receptor genes respectively. Similar sequences are also located in the terminal regions of other Herpes viruses (data not shown), suggesting that these V(D)J RSS like sequences may define a recombination pathway common to all Herpes viruses.

The present inventors considered the possibility that the DBP might be viral homologs of the RAG proteins by several coincidences in gene structure, gene regulation and protein structure between the DBP and the RAG proteins. The RAG genes are notable for their lack of introns within the coding sequences, an unusual feature shared with the genes encoding the DBP. The close proximity of RAG-1 and RAG-2 in the vertebrate genome is consistent with the origin of the RAG via integration and duplication of a DBP-like gene in the vertebrate germ line genome. A pattern of inversions in genomic orientation flanking the DBP genes in Herpes simplex (ICP8) and EBV (BALF2) has also been described, and integration of EBV DNA into the host chromosome occurs at a high rate during viral replication.

Analysis of BALF2 promoter sequences suggests a consensus CRE (cyclic AMP response element) is present, and suggests that BALF2 expression may be regulated by cAMP (data not shown). Similarly the RAG genes are regulated by cAMP. Thus, shared promoter sequences and regulatory pathways between the DBP genes and RAG may account for the observed modulation of endogenous RAG gene expression during EBV infection in B lymphocytes.

As demonstrated for the first time herein, the D35E-like regions of both RAG proteins are located within a functional core of the proteins required for V(D)J recombination. As shown in FIG. 1, the location of the BALF2 D35E like region (and other DBP motifs) is similar to the location of the RAG-1 D35E-like region both with respect to a conserved interval of approximately 200 amino acids between the respective zinc finger sites of BALF2 (BALF2 protein zinc finger site identified via similarity to the confirmed zinc finger region of Herpes simplex ICP8) and RAG-1, as well as the location of the respective motifs at a similar interval from the amino and carboxyl portions of the molecule.

Example 3

The following example illustrates the identification, expression and purification of BALF2 and RAG-2 putative site-specific DNA binding regions as glutathione binding proteins.

When the D35E region of the Tcl transposase TcA is included in the alignment of BALF2 and the RAG protein D35E-like regions (FIG. 1), it is apparent that the site-specific binding region of TcA overlaps a region of the RAG proteins and the DBP. This region of the RAG proteins, like the previously noted D35E-like regions of both RAG proteins, is located within a functional core of the proteins required for V(D)J recombination. To date, while genetic evidence has suggested that a region of RAG-1 protein interacts with the sequences flanking the V(D)J RSS, prior to the present invention, no V(D)J specific binding region of the RAG proteins has been identified.

Therefore, the putative site-specific binding regions of the BALF2 and RAG-2 proteins shown in FIG. 1 were expressed for characterization in in vitro binding assays. The BALF2 amino acids 440–639 (encoded by plasmid BA506/306 and denoted pBA506/306) and RAG-2 amino acids 1–201 (encoded by plasmid R2502/302 and denoted pR2502/302) glutathione S transferase fusion proteins are soluble when expressed in E. coli and are readily isolated on glutathione agarose. For use in EMSA binding studies, pBA506/306 and pR2502/302 were additionally purified via digestion with thrombin to remove the 27 kd glutathione binding amino terminus.

Regions of BALF2 and RAG-2 protein which the present inventors aligned with the site-specific binding region of the Tcl transposase (See FIG. 1) were expressed in *E. coli* and purified as fusion proteins with glutathione S-transferase using the PGEX-2T vector (Smith and Johnson 1988). Fusion proteins were designed to include the putative binding regions of the BALF2 and RAG-2 proteins in the absence of the D35E-like region which contribute non-specific DNA binding activity to the Tc transposases.

DNA encoding the entire BALF2 DNA (obtained from T. Ooka, CNRS Lyon, France) was amplified using Pfu polymerase (Stratagene) to generate a DNA fragment encoding BALF2 amino acids 440–639 (representing the region including the site-specific DNA binding site) inclusive with BamHI (5') and EcoRI (3') restriction sites using primers denoted herein as SEQ ID NO:17 and and SEQ ID NO:18. This BamHI/EcoRI fragment was cloned into the PGEX-2T BamHI/EcoRI restriction site to generate plasmid BA506/306. A putative zinc finger site in BALF2, denoted herein as SEQ ID NO:19 (aa 453–466) identified via comparison with the Herpes simplex ICP8 protein was included in the fusion protein.

DNA encoding murine RAG-2 protein amino acids 1–201 inclusive was also amplified with Pfu polymerase and cloned into the PGEX-2T vector BamHI/EcoRI restriction site using primers denoted herein as SEQ ID NO:20 and SEQ ID NO:21 to generate plasmid R2502/302. Identity of expressed coding regions in plasmids BA506/306 and R2502/302 was confirmed by restriction analysis of the plasmids and by the ability of the respective plasmids to express a correctly sized fusion protein in IPTG induced *E. Coli* demonstrated by PAGE gel electrophoresis (data not shown). A plasmid comprising the entire BALF2 coding region was cloned into the pcDNA1/Amp vector HindIII/XbaI restriction site using primers denoter herein as SEQ ID NO:29 and SEQ ID NO:30 to generate plasmid BA5001/3001.

Example 4

The following example demonstrates that a binding site-specific for V(D)J RSS and related V(D)J RSS like sequences such as EV(D)J exists within BALF2 protein and the corresponding region of RAG-2 protein.

In this experiment, V(D)J RSS double stranded oligonucleotides corresponding the immunoglobulin heptamer 12 space nonamer, immunoglobulin 23 space nonamer and EV(D)J putative RSS were designed. These oligonucleotides are of similar size and base composition, and do not contain any sequences not directly contained within the putative RSS.

Purified proteins used for Electrophoresis Mobility Shift Assay (EMSA) analysis were generated by isolation of fusion protein from *E coli* on glutathione sepharose (Pharmacia). Purified protein was eluted from glutathione sepharose with distilled water, and digested with thrombin for removal of glutathione S-transferase (Smith and Johnson, 1988). Following thrombin cleavage, protein concentration and stability was assessed via SDS PAGE (data not shown), and proteins were stored in aliquots at −70° C. prior to use. For the EMSA analysis, oligonucleotides used in the assay encoding canonical 12 and 23 bp spacer V(D)J RSS (V(D)J RSS sequences (Hesse et al., 1990) and EV(D)J sequences are denoted herein as SEQ ID NO:22 (VDJ54), SEQ ID NO:23 (VDJ34), SEQ ID NO:24 (VDJ56), SEQ ID NO:25 (VDJ36), SEQ ID NO:26 (EVDJ51) and SEQ ID NO:27 (EVDJ31). VDJ54 and VDJ34 were annealed to form the double stranded oligonucleotide VDJ54/34 corresponding to the V(D)J 12 bp spacer RSS. VDJ56 and VDJ36 were annealed to form the double stranded oligonucleotide VDJ56/36 corresponding to the V(D)J 23 bp spacer RSS. EVDJ51 and EVDJ31 were annealed to form the double stranded oligonucleotide EVDJ51/31 corresponding to the EV(D)J sequence identified in this example.

Double stranded oligonucleotides were labeled with T4 polynucleotide kinase (Promega) and gamma P32 labeled ATP (Amersham, 3000 mCi/mM) and purified from incorporated nucleotides via a Pharmacia "Quikspin' Column. Incubation of oligonucleotides with protein was in binding buffer. Poly DIC was added to binding buffer at a concentration of 1 ng/lambda, and sodium chloride concentration in binding buffer was 180 mM. Zinc sulfate and magnesium chloride were added to binding buffer at final concentrations of 5 mM and 3 mM respectively. Following 10 minutes binding at 22° C., binding reactions were electrophoresed on 8% native acrylamide gels in 0.2× TBE buffer at 4° C. Short electrophoresis times (90 minutes) at 10 volts/cm were utilized to minimize protein/DNA disassociation which was evident during longer electrophoresis times (data not shown).

Using a high salt buffer required for detection of transposase TcA site-specific binding to Tc element termini and electrophoresis in low ionic strength buffer (0.2× TBE) complexes between the V(D)J RSS and related EV(D)J oligonucleotides and the putative binding sites of BALF2 protein and RAG-2 protein were resolved. The specificity of these complexes is evident by the variable intensity of complexes formed between immunoglobulin heptamer 12 space nonamer, immunoglobulin 23 space nonamer and EV(D)J putative RSS using identical reaction conditions and pBA506/306. In addition, no binding to a consensus AP1 oligonucleotide by either pBA506/306 or pR2502/302 is evident under these conditions (data not shown).

Remarkably, the complex formed by pBA506/306 on the V(D)J heptamer-12 spacer-nonamer RSS in the presence of 5 mM zinc sulfate is much more readily detectable than the complex between either the EV(D)J sequence or the V(D)J heptamer-23 spacer-nonamer. This result, which has proven readily reproducible in several independent experiments is unanticipated because it was expected that site-specific binding would be maximal between the BALF2 protein and a V(D)J like sequence present within its own genome. These experiments were also repeated with a second EV(D)J specific oligonucleotide extended to include a second nonamer-like sequence which is located 3' to the nonamer-like sequence denoted as SEQ ID NO:28. An increase in specific pBA506/306 binding to the extended EV(D)J sequence in the presence of zinc sulfate was noted with levels comparable to binding to the V(D)J heptamer-23 spacer oligonucleotide (data not shown). However, binding of pBA506/306 to both the EV(D)J sequence and the V(D)J heptamer-23 spacer-nonamer was in all cases much less readily detectable than binding to the V(D)J heptamer-12 spacer-nonamer.

pR2502/302 binds most readily, although less than pBA506/306, to the V(D)J heptamer-12 spacer-nonamer in the presence of 5 mM zinc. However, in contrast to pBA506/306 which appears to have reduced binding to all three target oligonucleotides in the presence of 3 mM Magnesium as an alternate divalent cation, or in the absence of any divalent cation, pR2502/302 appears to have weak but increased binding to both the EV(D)J oligonucleotide and the V(D)J heptamer-23 spacer-nonamer in the presence of 3 mM magnesium as a divalent cation, while binding to the V(D)J heptamer12 spacer-nonamer is reduced. The approximate positions of the above referenced recombinant molecules relative to the entire BALF2 coding region is shown in FIG. 3.

These differential effects are not due to trace bacterial protein contamination of the recombinant protein or other bacterial DNA binding activity for two reasons. First, any trace bacterial proteins responsible for these effects would be present in both the BALF2 and RAG-2 recombinant protein preparations, and thus could not account for the differential binding effects described above since the identically prepared bacterial extracts differ only in the expression of BALF2 or RAG-2 fusion proteins. Second, these binding patterns are not seen when the oligonucleotides are incubated with IPTG induced E. coli/PGEX-2T extracts co-purified and thrombin digested with the protein extracts, or with glutathione reductase in the absence of BALF2 or RAG-2 fusions (data not shown). Based upon these results, the present inventors have shown that a component of a site-specific V(D)J RSS binding activity is present in both the BALF2 and RAG-2 fusion proteins described in the present invention. It is an embodiment of the present invention to optimize the binding parameters of the BALF2 and RAG proteins to V(D)J and V(D)J-like sequences and identify the specific DNA/protein sites involved in this binding. For instance, in spite of relatively large amounts of pure protein in the binding reactions (10 ng per binding reaction) relative to oligonucleotide (0.01 ng per reaction) (molar ratio approximately 50:1) the formation of complexes relative to free oligonucleotides is low using these binding and electrophoresis conditions. pBA506/306 and pR2502/302 may partially precipitate in the high salt conditions used for binding (data not shown), conditions which were chosen primarily based upon previous experiments with the invertebrate TcA transposase. Additionally, the binding regions which we have characterized in this work may be lacking additional stabilizing regions or modifications present in the full length protein as expressed in vertebrate cells, a hypothesis which can be tested by expression of these regions of BALF2 and RAG-2 protein in vertebrate rather than bacterial cells.

The 12/23 spacer rule for V(D)J recombination of immunoglobulin RSS is observed only in the presence of magnesium ion as a divalent cation. The binding studies described above support a model of V(D)J recombination in which divalent cations binding to the BALF and RAG proteins play an important role in the recognition of RSS, and, without being bound by theory, also suggest that the RAG-1 and RAG-2 proteins both have arisen via insertion and duplication of a Herpes DBP like precursor molecule into the vertebrate germ line genome.

Figure 2:
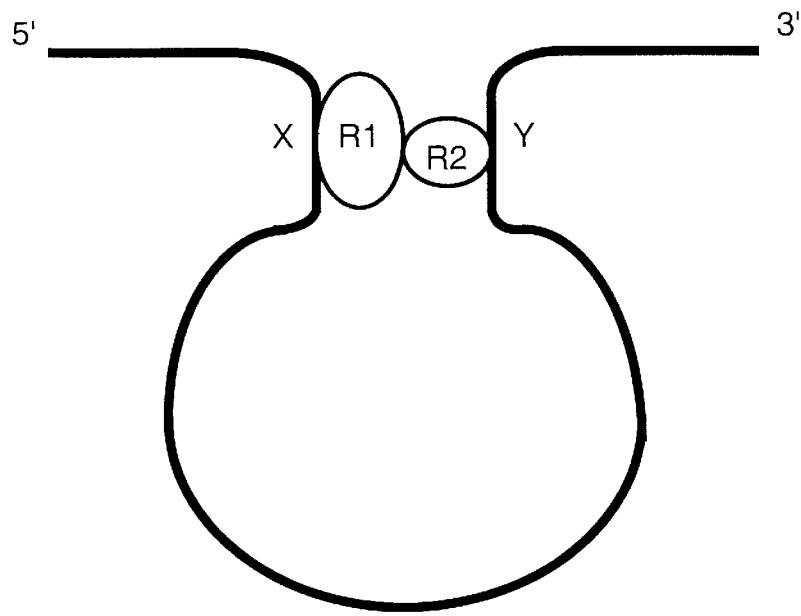
FIG. 2 is a schematic drawing of a model of a homodimeric recombinase complex of BALF2 protein with EBV terminal sequences and of RAG-1 with RAG-2 proteins.
Figure 2:
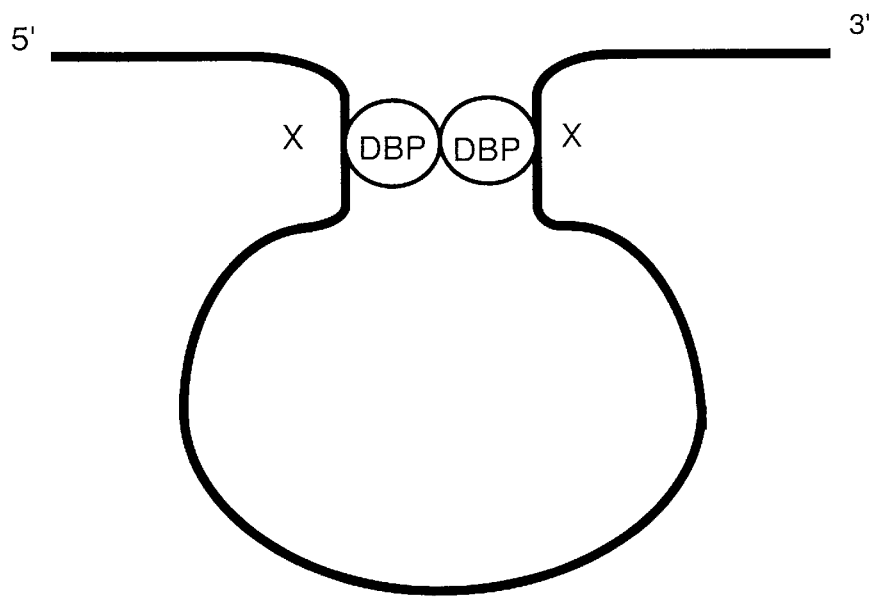

Without being bound by theory, the present inventors propose a model shown in FIG. 2. In this model, a homodimeric recombinase complex of BALF2 protein with EBV terminal sequences such as EV(D)J (lower panel) has been modified giving rise to a heterodimeric recombination complex of the RAG-1 and RAG-2 proteins (upper panel), each RAG protein binding preferentially with one of the two distinct (12 spacer and 23 spacer) V(D)J heptamer nonamer RSS. The data shown herein suggest that the RAG-2 protein preferentially associates with the 23 spacer RSS in the presence of magnesium ion, while the BALF2 protein which is more structurally similar to the RAG-1 protein binds preferentially to the 12 spacer RSS in the presence of zinc. The zinc finger domain of both BALF2 and RAG-1 in this model would then serve to increase the local zinc concentration in the region of the binding site of the BALF2 and RAG-2 proteins respectively and stabilize interactions with the 12 bp spacer RSS. Although the zinc site is dispensable in V(D)J recombination in the presence of high (non-physiologic) RAG-1 concentrations, and is not absolutely required for Herpes virus replication with high DBP concentrations, under physiologic conditions these respective zinc binding sites would potentially play a critical role in regulation the recombination rate and specificity. Conversely, the RAG-2 protein which lacks a canonical zinc binding site would tend to preferentially bind to magnesium in this model, thus favoring interactions with the 23 bp spacer and accounting for the 12/23 bp spacer rule.

This model of RAG protein function has important implications for retroviral pathogenesis. Alteration of the RAG recombination complex via substitution of one of the RAG proteins by a retroviral integrase monomer may alter V(D)J regulation and target site selection, and may account for the altered T cell receptor repertoire found in retroviral diseases such as AIDS. In view of the ongoing efforts to develop inhibitors of the HIV-1 integrase for therapy of HIV-related illnesses, a conserved recombinase core shared between RAG-1, RAG-2 and molecules such as the HIV integrase may complicate efforts to develop pharmaceutical agents active against HIV-1, as these drugs could be at the same time immunosuppressive, being targeted to the V(D)J recombinase. It is also possible that synthetic peptides corresponding to the D35E-like regions of the RAG proteins could have anti-viral properties via interference with the HIV1 integrase.

Based upon similar D35E-like regions, protein organization, gene structure, and functional properties, it is proposed herein that BALF2 and other DBP are viral homologues of the RAG proteins. Alignment of the D35E-like regions of the Tc family transposases, the DBP, and the RAG proteins suggests that all these proteins may share an analogous site-specific DNA binding region, and the present inventors show that this site-specific DNA binding region of BALF2 and RAG proteins exhibits specific binding to V(D)J immunoglobulin recombination signals in vitro. Specificity of this V(D)J signal binding activity appears sensitive to divalent cations, consistent with functional properties of the RAG proteins. The present inventors believe that RAG-like extra chromosomal sequences (RAGLES) such as the herpes DBP activate recombination of viral V(D)J-like sequences in a manner similar that of RAG activation of cellular V(D)J signals. Interactions between the RAG and RAGLES may lead to altered T cell and B cell repertoire as a result of disregulation of V(D)J recombination, a mechanism leading to virus induced auto-immunity and lymphoproliferation.

What is claimed is:

1. An isolated peptide consisting of a sequence selected from the group consisting of SEQ ID NOS:5–12, SEQ ID NOS:31–32, and homologue sequences, which homologue sequences have the identifying characteristics of:

(a) an initial and terminal amino acid residue, each of said residues being selected from the group consisting of aspartate and glutamate, said initial and terminal amino acid residues being separated by approximately 34 to 39 amino acid residues; and, (b) alignment with the sequence *NXXXXXXSXXX-WLKXXXXXXXXXXXXXXAXXGXLXAX* (SEQ ID NO:2), wherein the probability of obtaining an observed number of aligned amino acid residues between said homologue sequences and SEQ ID NO:2 is p<0.05, wherein said probability is determined using an alignment algorithm as follows:

(1) said initial and terminal amino acid residues of said homologue sequences are aligned with SEQ ID NO:2 amino acid residues denoted by an asterisk, wherein said residues denoted by an asterisk are an amino acid residue selected from the group consisting of aspartate and glutamate;

(2) amino acid residues between said initial and terminal residues of said homologue sequences are aligned with SEQ ID NO:2, and said observed number of aligned amino acid residues between said homologue sequences and SEQ ID NO:2 is determined according to the following criteria:

(i) spacing of amino acid residues in SEQ ID NO:2 is not altered;

(ii) insertion of spaces or deletion of amino acid residues in said homologue sequences is permitted;

(iii) non-conserved amino acids (X) in SEQ ID NO:2 are included as non-matching characters;

(iv) an amino acid residue in said homologue sequences which is in approximately the same position as a non-X amino acid residue in SEQ ID NO:2 is matched with said non-X amino acid residue if said non-X amino acid residue in said homologue sequences is a member of a group of similarity default amino acids for said non-X amino acid residue, wherein the groups of similarity default amino acids are as follows:

a. neutral/weakly hydrophobic amino acid residues: P, A, G, S, and T;

b. acidic/hydrophilic amino acid residues: Q, N, E, B, D, and Z;

c. basic/hydrophilic amino acid residues: H, K, and R;

d. hydrophobic/aliphatic amino acid residues: L, I, V, and M;

e. hydrophobic/aromatic amino acid residues: F, Y, and W; and, f. C amino acid residues; and, (3) said probability of obtaining an observed number of aligned amino acid residues between said homologue sequence and SEQ ID NO:2 is determined by generating a distribution of 1500 random sequences of amino acid residues between said initial and terminal amino acid residues of said homologue sequences by insertion of spaces or deletion of amino acid residues, and the percentage corresponding to said observed number of aligned amino acid residues is identified.

2. An isolated peptide consisting of a sequence selected from the group consisting of SEQ ID NOS:5–12 and SEQ ID NOS:31–32.

* * * * *